United States Patent
Furuhashi et al.

(10) Patent No.: US 9,872,951 B2
(45) Date of Patent: Jan. 23, 2018

(54) BLOOD PURIFICATION APPARATUS AND PRIMING METHOD FOR THE SAME

(71) Applicant: Nikkiso Company Limited, Tokyo (JP)

(72) Inventors: Tomohiro Furuhashi, Shizuoka (JP); Satoshi Takeuchi, Shizuoka (JP); Akira Sugioka, Shizuoka (JP); Masahiro Toyoda, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 293 days.

(21) Appl. No.: 14/615,839

(22) Filed: Feb. 6, 2015

(65) Prior Publication Data

US 2015/0151036 A1  Jun. 4, 2015

Related U.S. Application Data

(63) Continuation of application No. PCT/JP2013/071511, filed on Aug. 8, 2013.

(30) Foreign Application Priority Data

Aug. 9, 2012 (JP) ................................. 2012-176901

(51) Int. Cl.
*A61M 1/36* (2006.01)
*A61M 1/34* (2006.01)
*A61M 1/16* (2006.01)

(52) U.S. Cl.
CPC ........ *A61M 1/3643* (2013.01); *A61M 1/3465* (2014.02); *A61M 1/3638* (2014.02);
(Continued)

(58) Field of Classification Search
CPC .............. A61M 1/1682; A61M 1/3465; A61M 1/3638; A61M 1/3643; A61M 1/3644;
(Continued)

(56) References Cited

U.S. PATENT DOCUMENTS

| 6,044,691 A | 4/2000 | Kenley et al. |
| 2010/0168640 A1 | 7/2010 | Kopperschmidt et al. |
| 2013/0035626 A1 | 2/2013 | Suzuki |

FOREIGN PATENT DOCUMENTS

| JP | 2010-273693 A | 9/2005 |
| JP | 2005-253555 A | 4/2006 |

(Continued)

OTHER PUBLICATIONS

Supplementary European Search Report dated Mar. 16, 2016, for Application No. PCT/JP2013071511.
(Continued)

*Primary Examiner* — John Kim
(74) *Attorney, Agent, or Firm* — The Dobrusin Law Firm, P.C.

(57) ABSTRACT

The present teachings provide a blood purification apparatus and a priming method, which can reduce or dispense with dedicated components used for automated priming and which can reduce manufacturing costs of a blood circuit while achieving the automated priming. The present teachings further provide a blood purification apparatus including a liquid level adjustment device that can optionally introduce or discharge air into or from an upper portion of a venous air trap chamber, a control device that can adjust a liquid level formed inside the venous air trap chamber to have the height at any desired position by operating the liquid level adjustment device, and a priming solution supplying line that can supply a priming solution to an arterial blood circuit and a venous blood circuit. As taught herein, during priming, the control device can fill the arterial blood circuit and the venous blood circuit with priming solution supplied from the priming solution supplying line by operating the liquid level adjustment device at any desired timing.

11 Claims, 29 Drawing Sheets

(52) U.S. Cl.
CPC ........ *A61M 1/3644* (2014.02); *A61M 1/3649* (2014.02); *A61M 1/3652* (2014.02); *A61M 1/1682* (2014.02); *A61M 1/365* (2014.02); *A61M 2205/3379* (2013.01)

(58) Field of Classification Search
CPC .. A61M 1/3649; A61M 1/365; A61M 1/3652; A61M 2205/3379
See application file for complete search history.

(56) References Cited

FOREIGN PATENT DOCUMENTS

| | | | |
|---|---|---|---|
| JP | 2007-282737 | A | 6/2008 |
| JP | 2010-000161 | A | 5/2009 |
| JP | 2012/139405 | A | 7/2012 |
| WO | 2005/118485 | A | 12/2005 |
| WO | 2011-099521 | A1 | 5/2011 |

OTHER PUBLICATIONS

Japanese Office Action, Application No. 2014-529557; dated May 10, 2017.

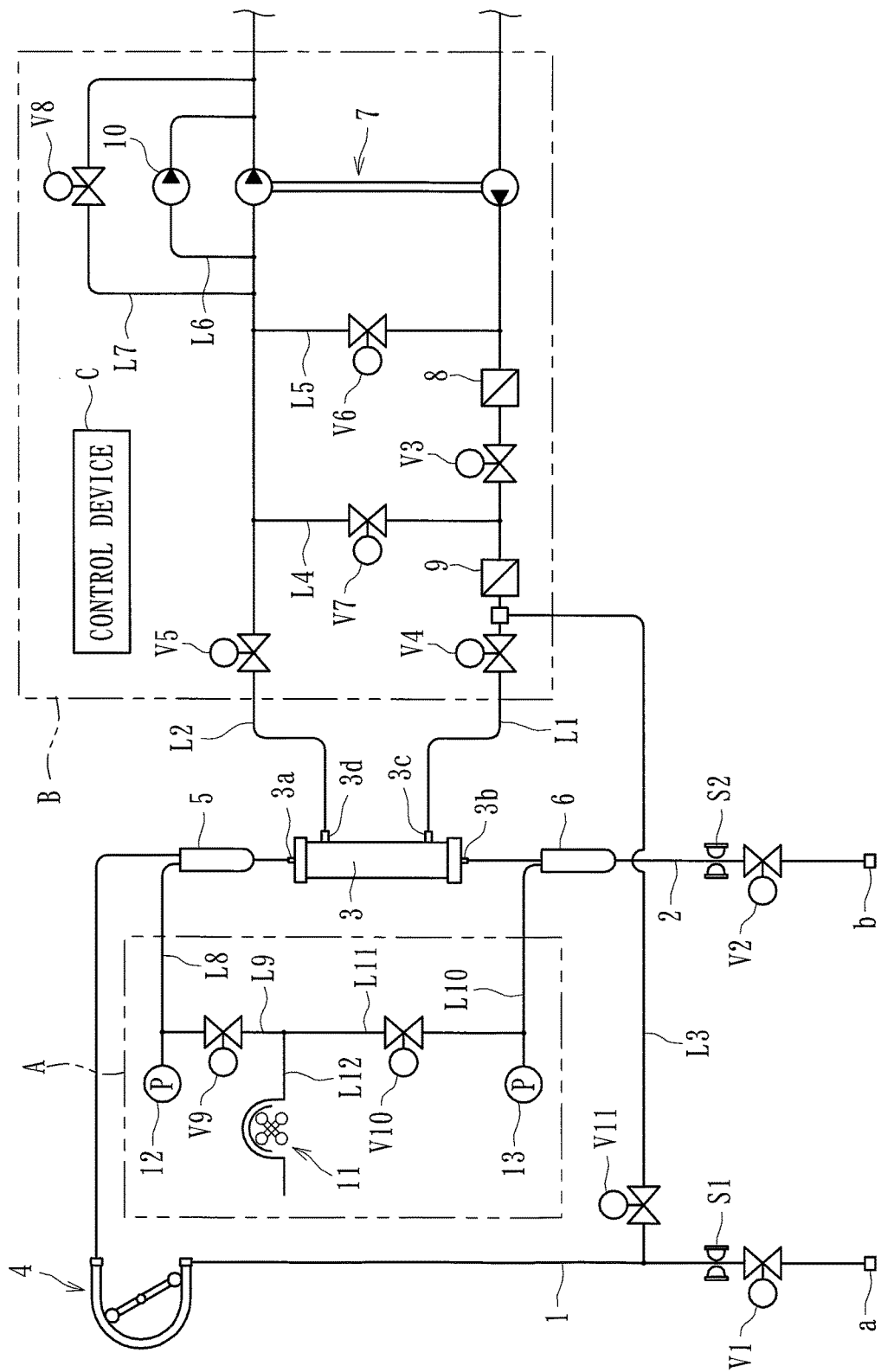
[Fig. 1]

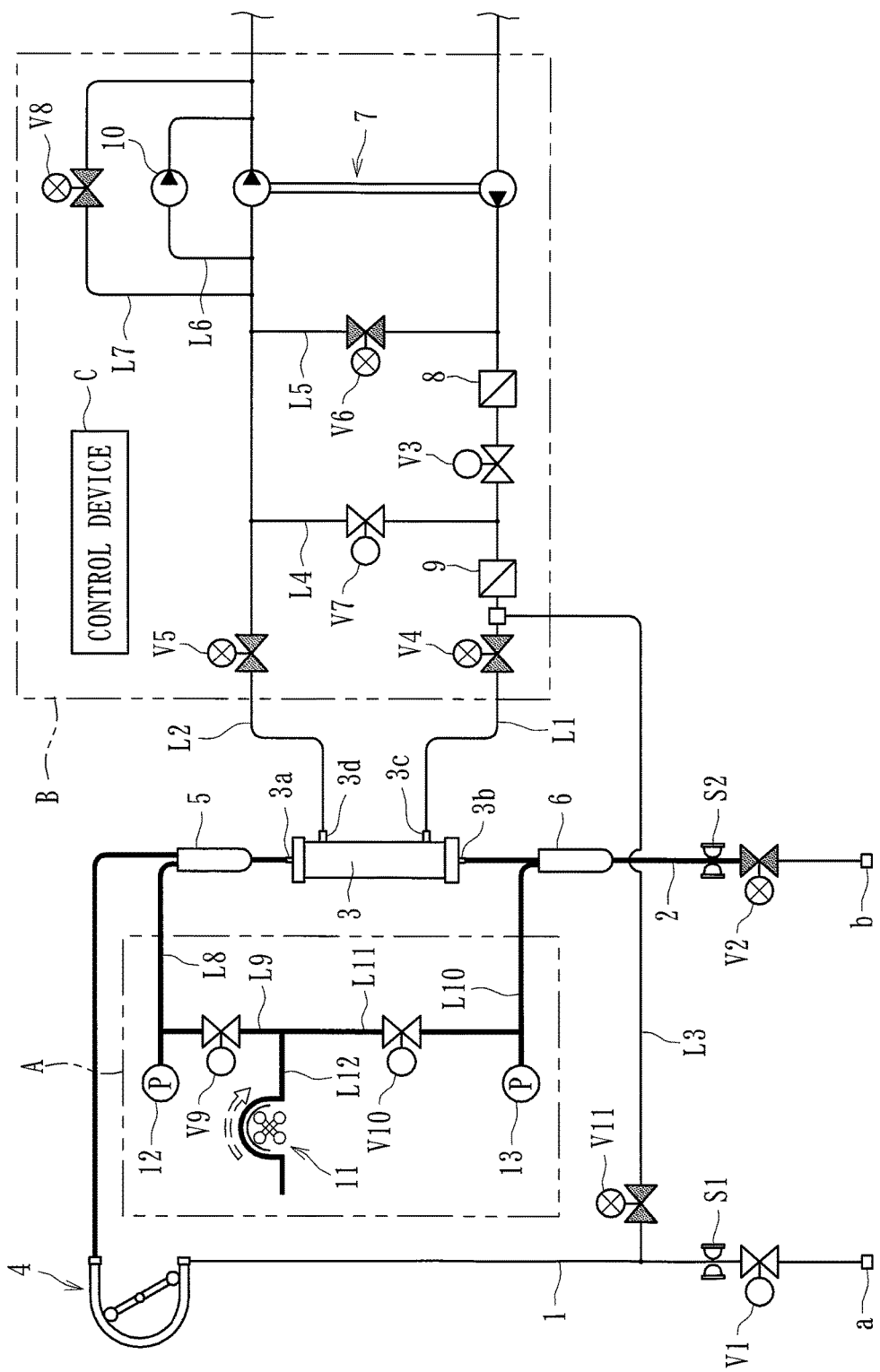
[Fig. 2]

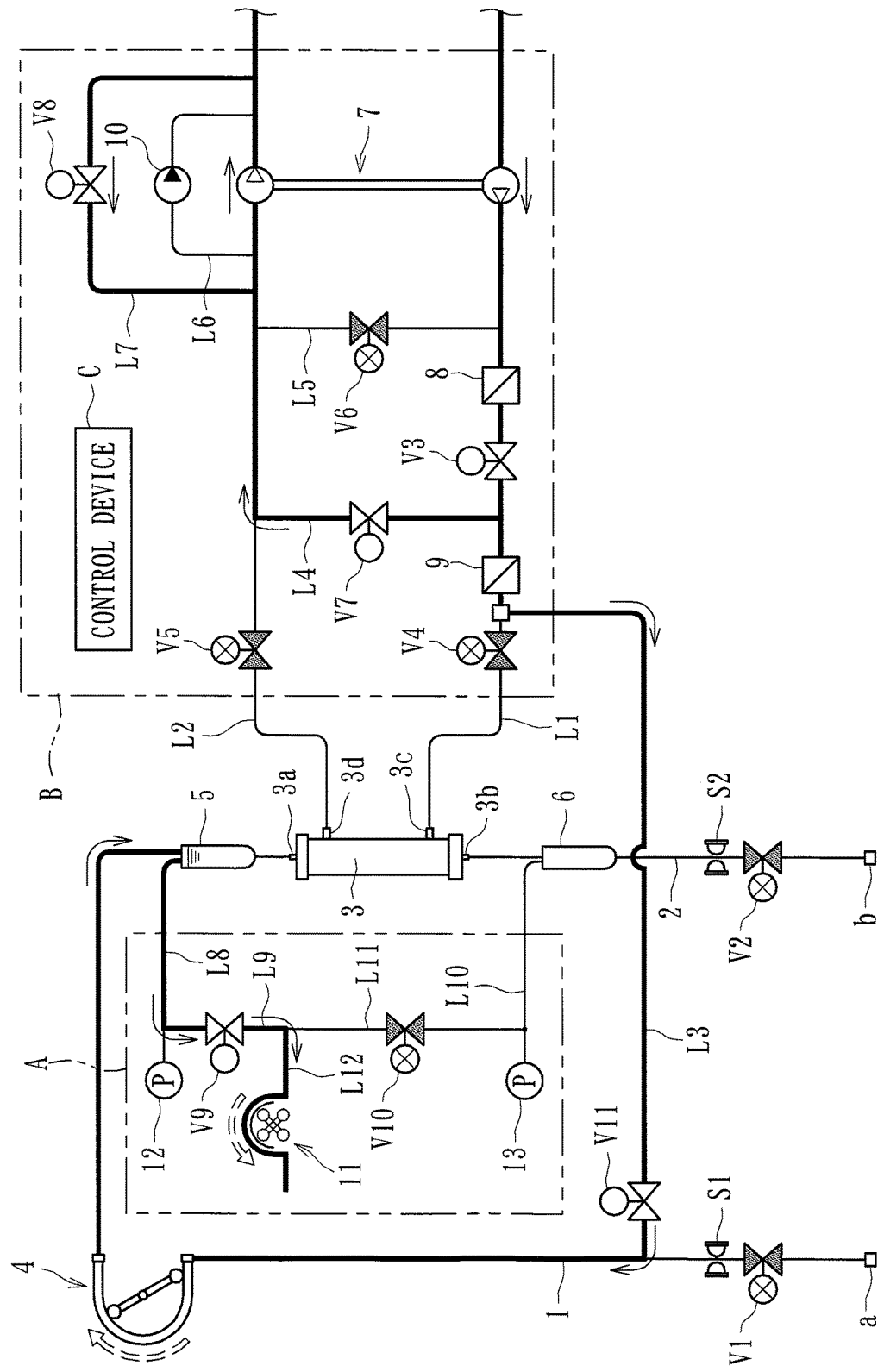
[Fig. 3]

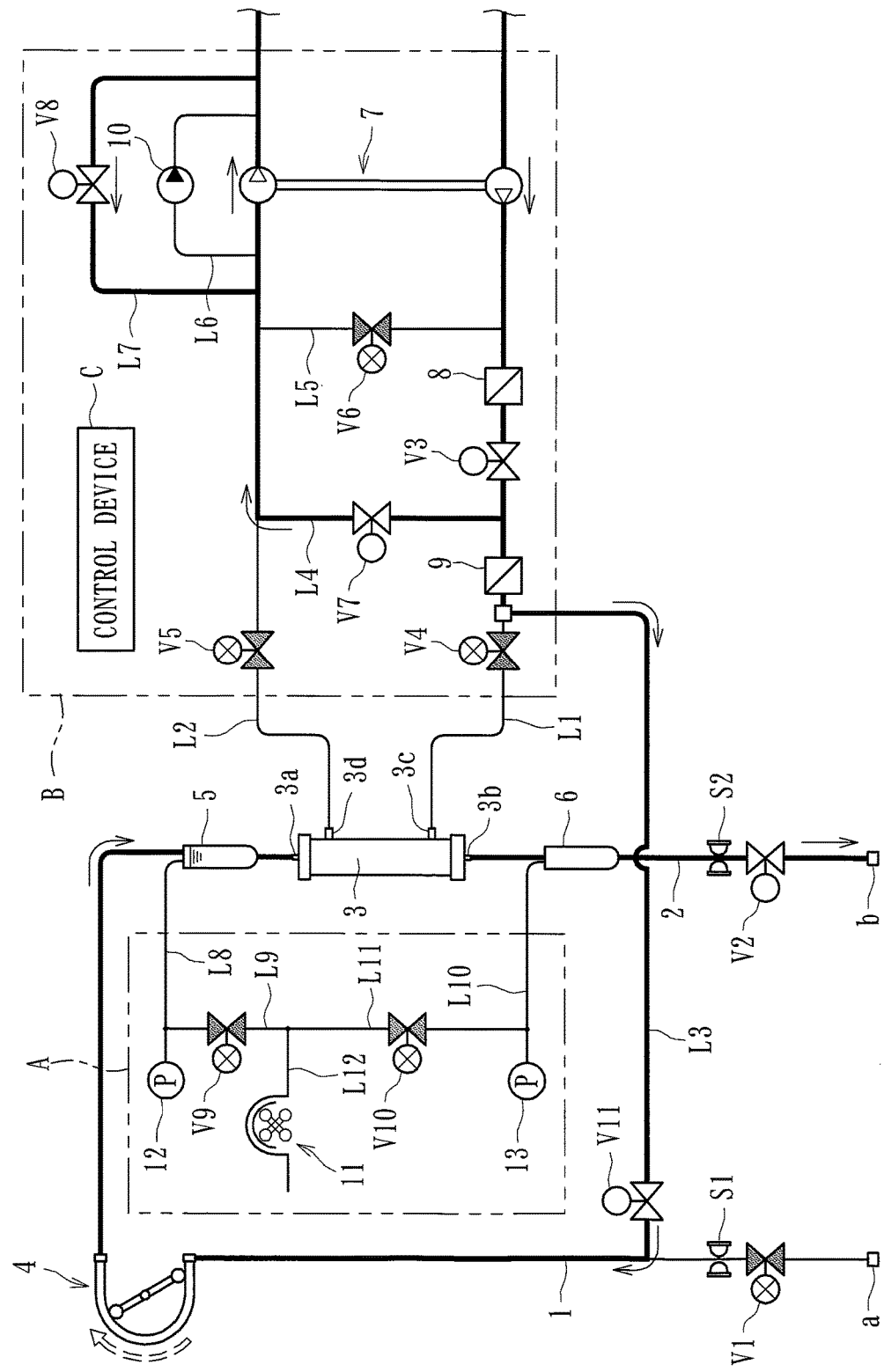
[Fig. 4]

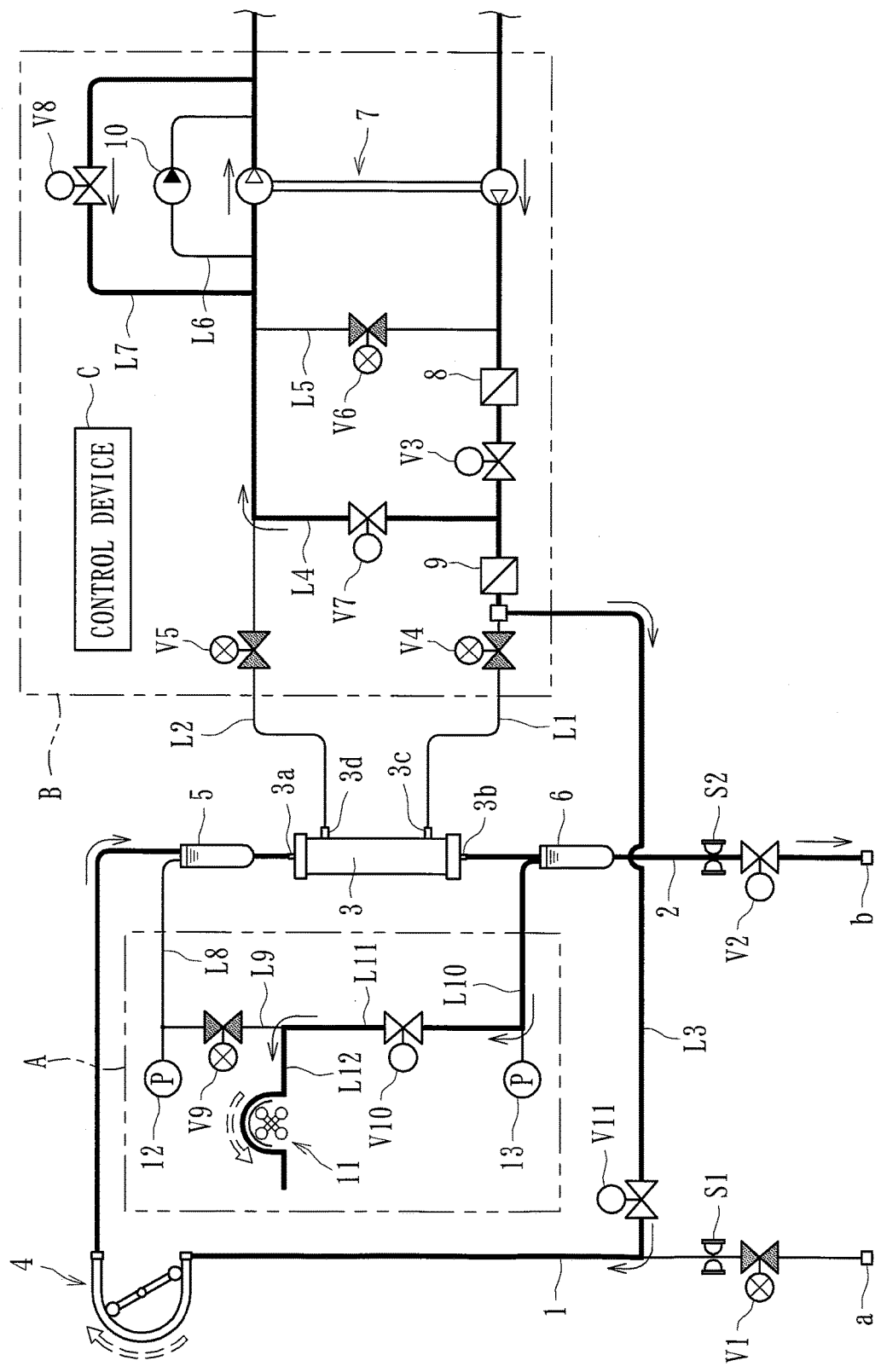
[Fig. 5]

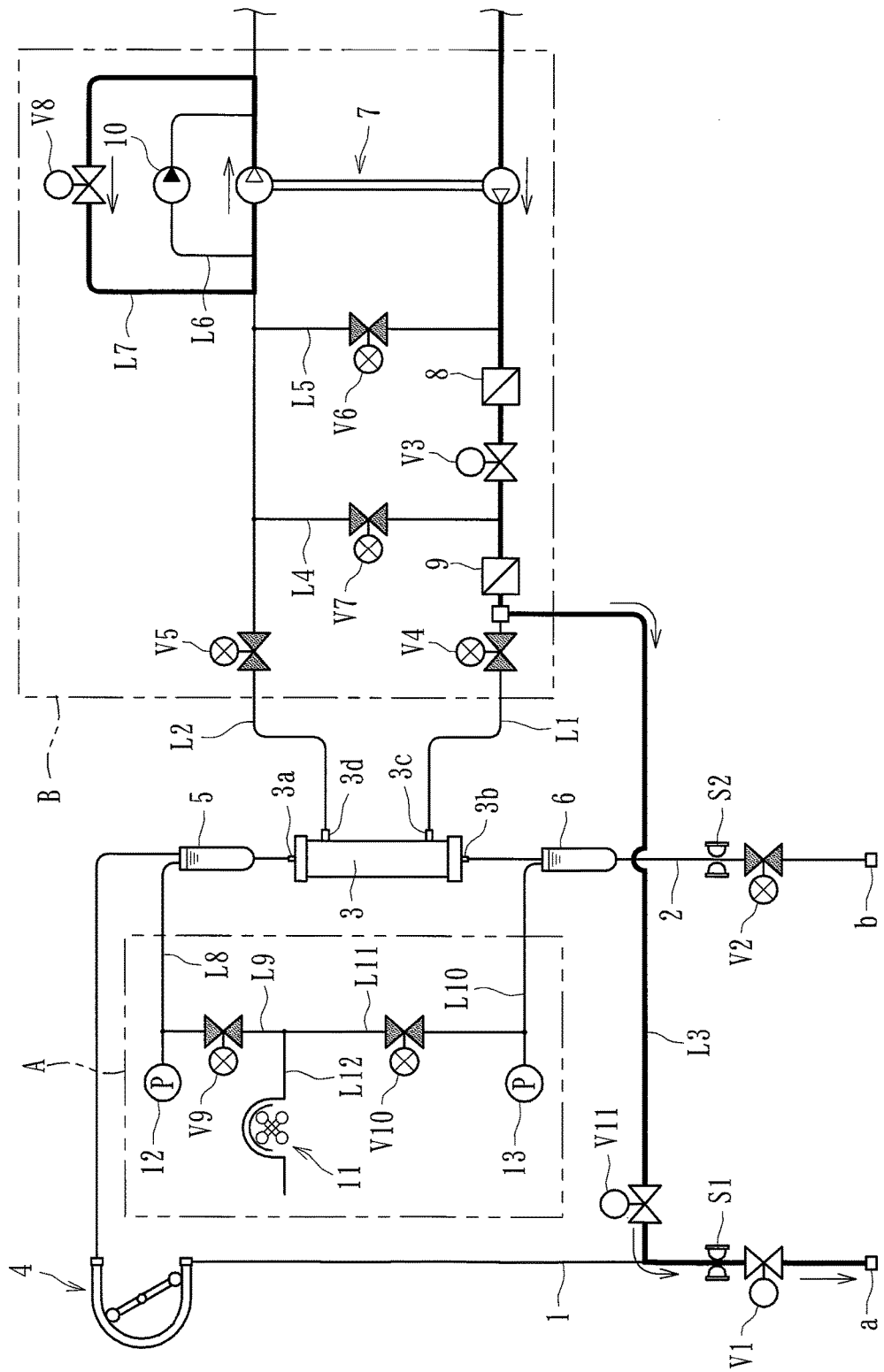
[Fig. 6]

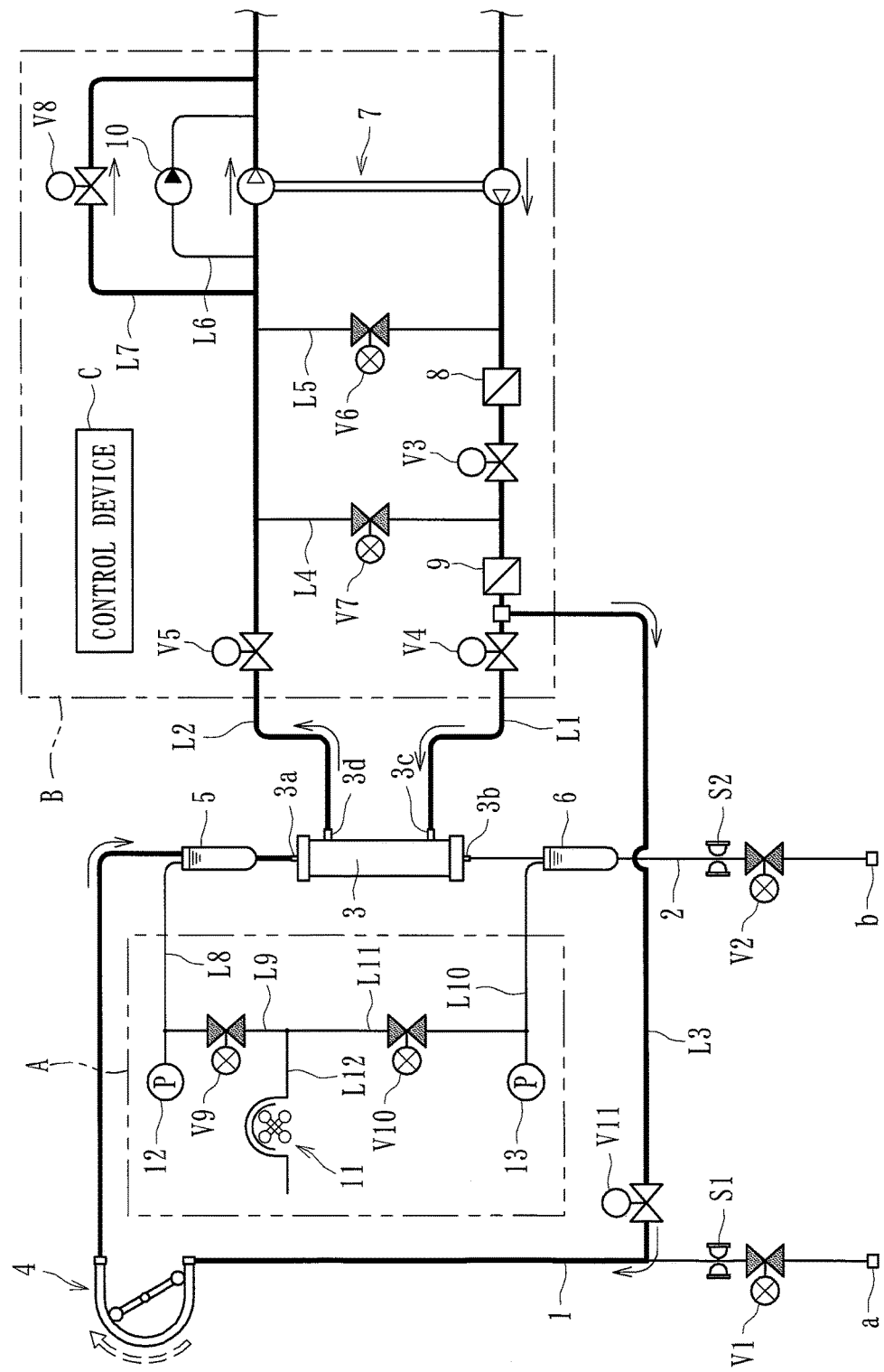
[Fig. 7]

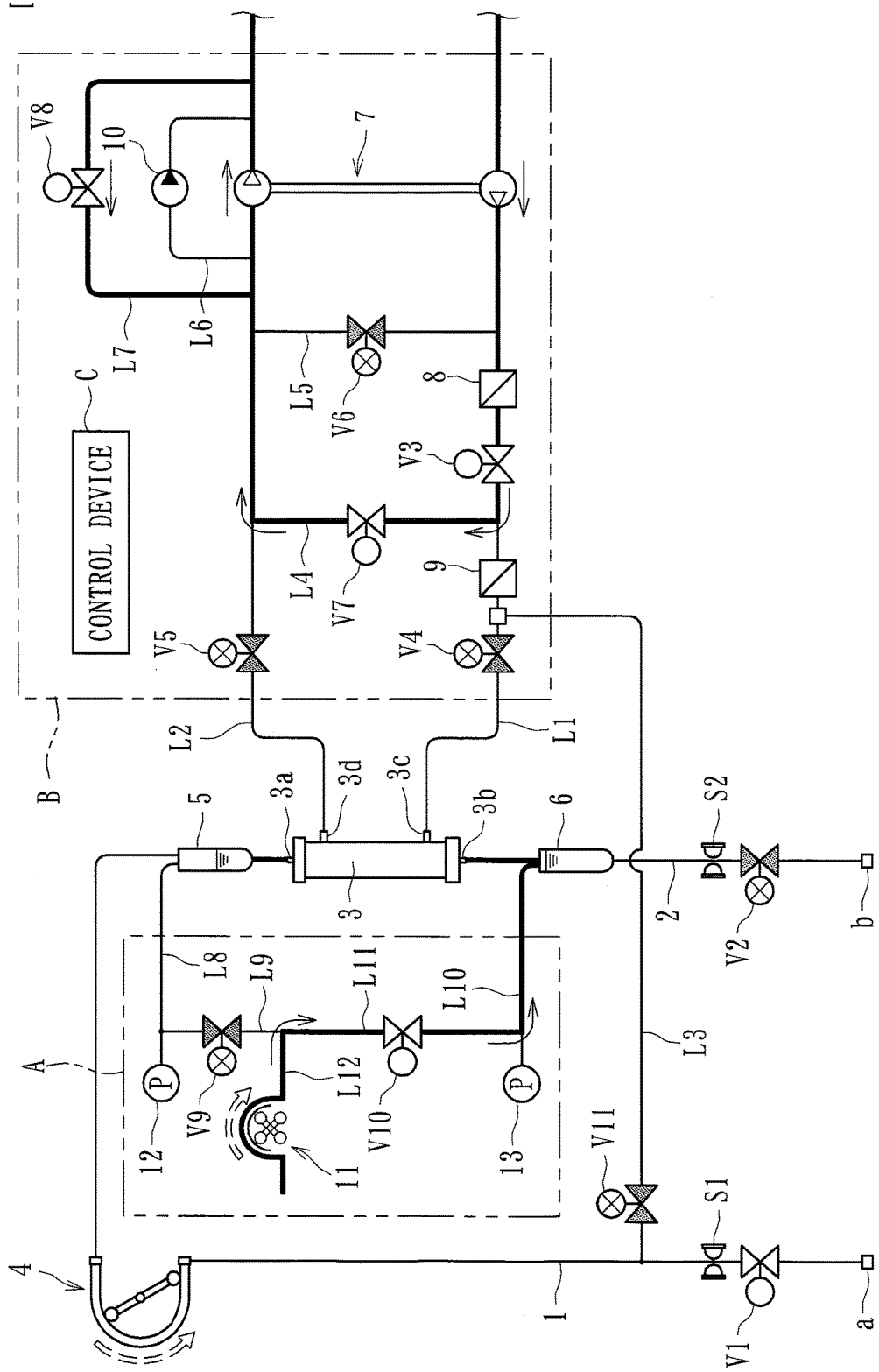

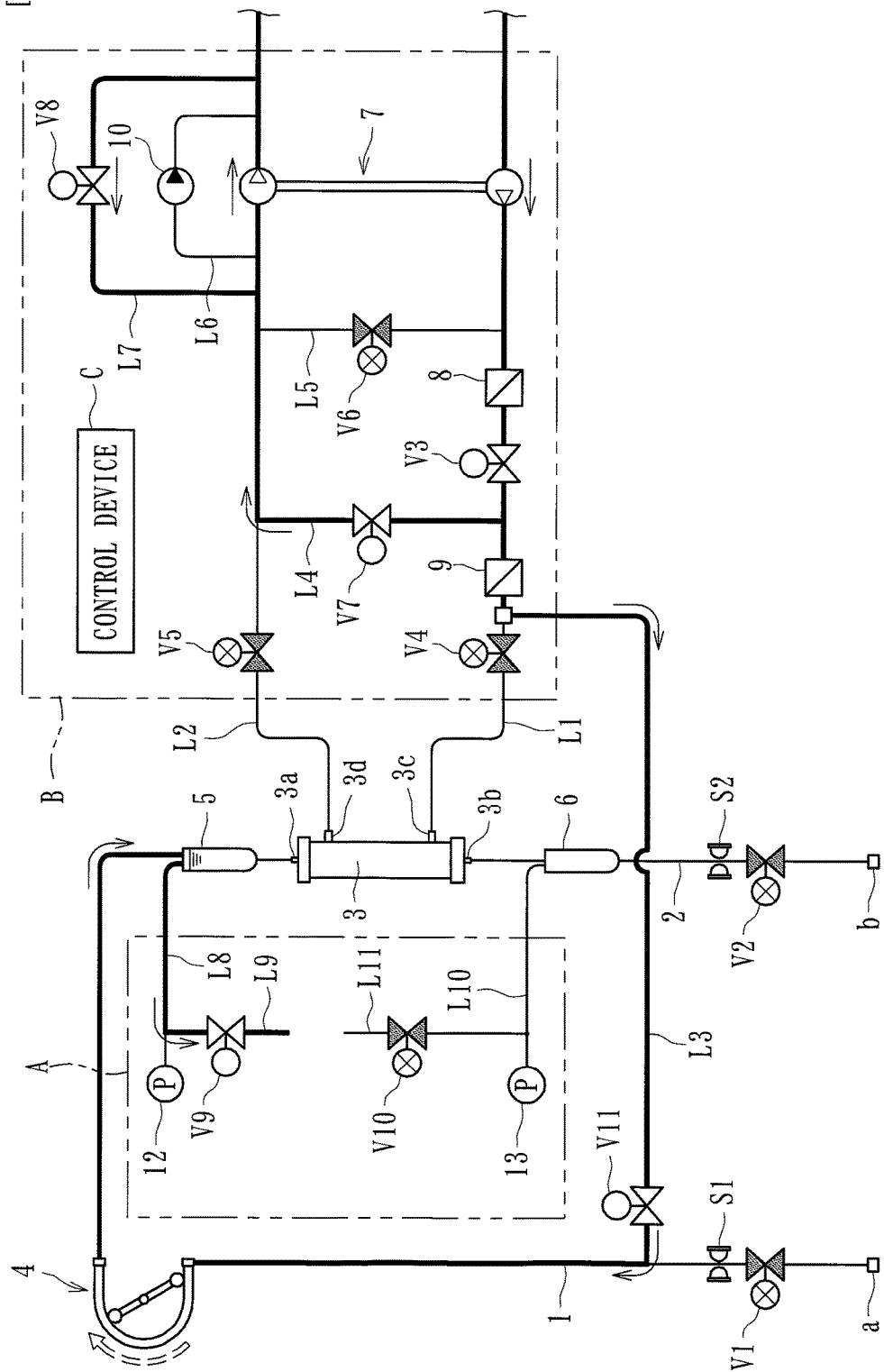

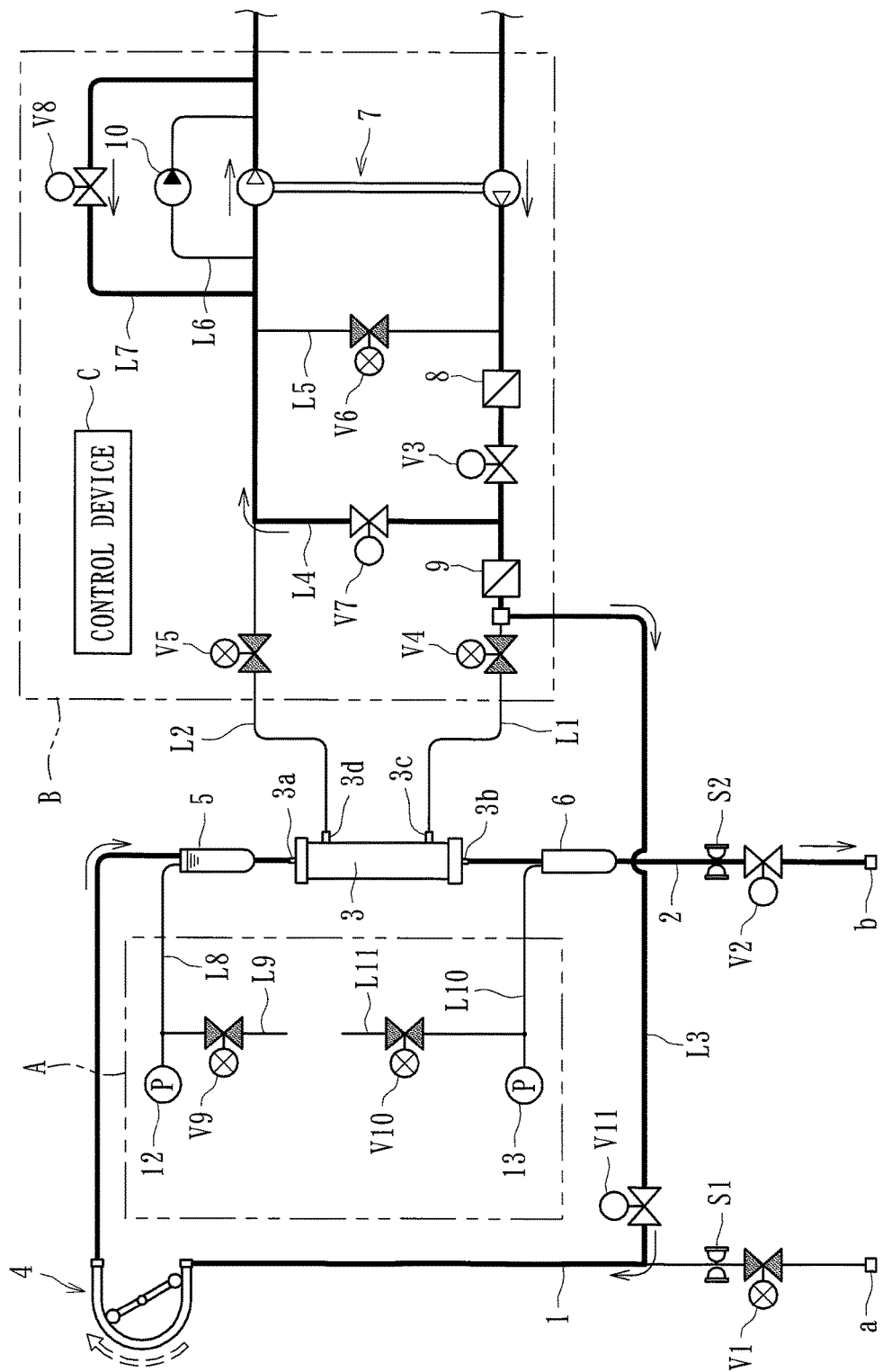

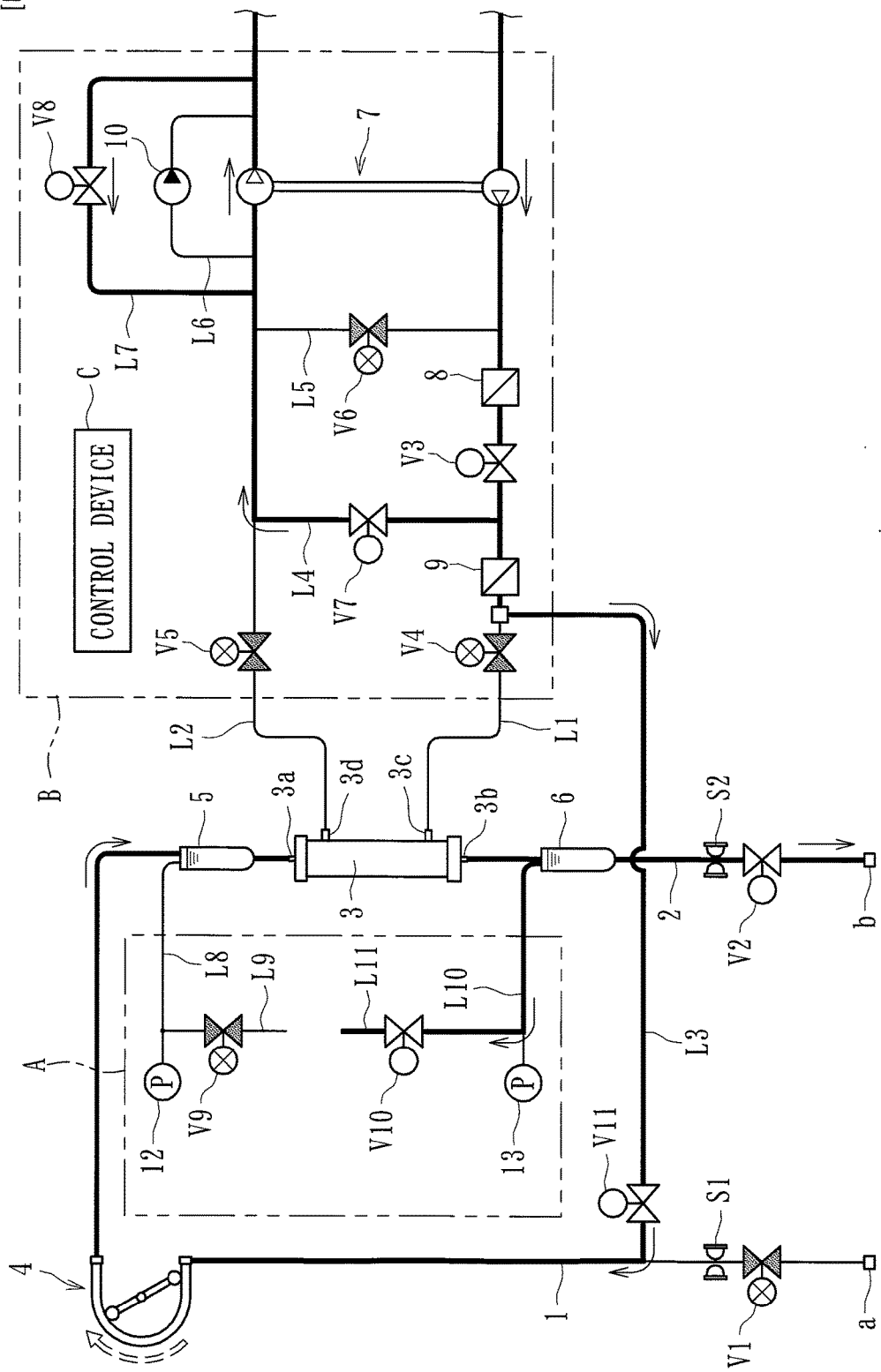
[Fig. 11]

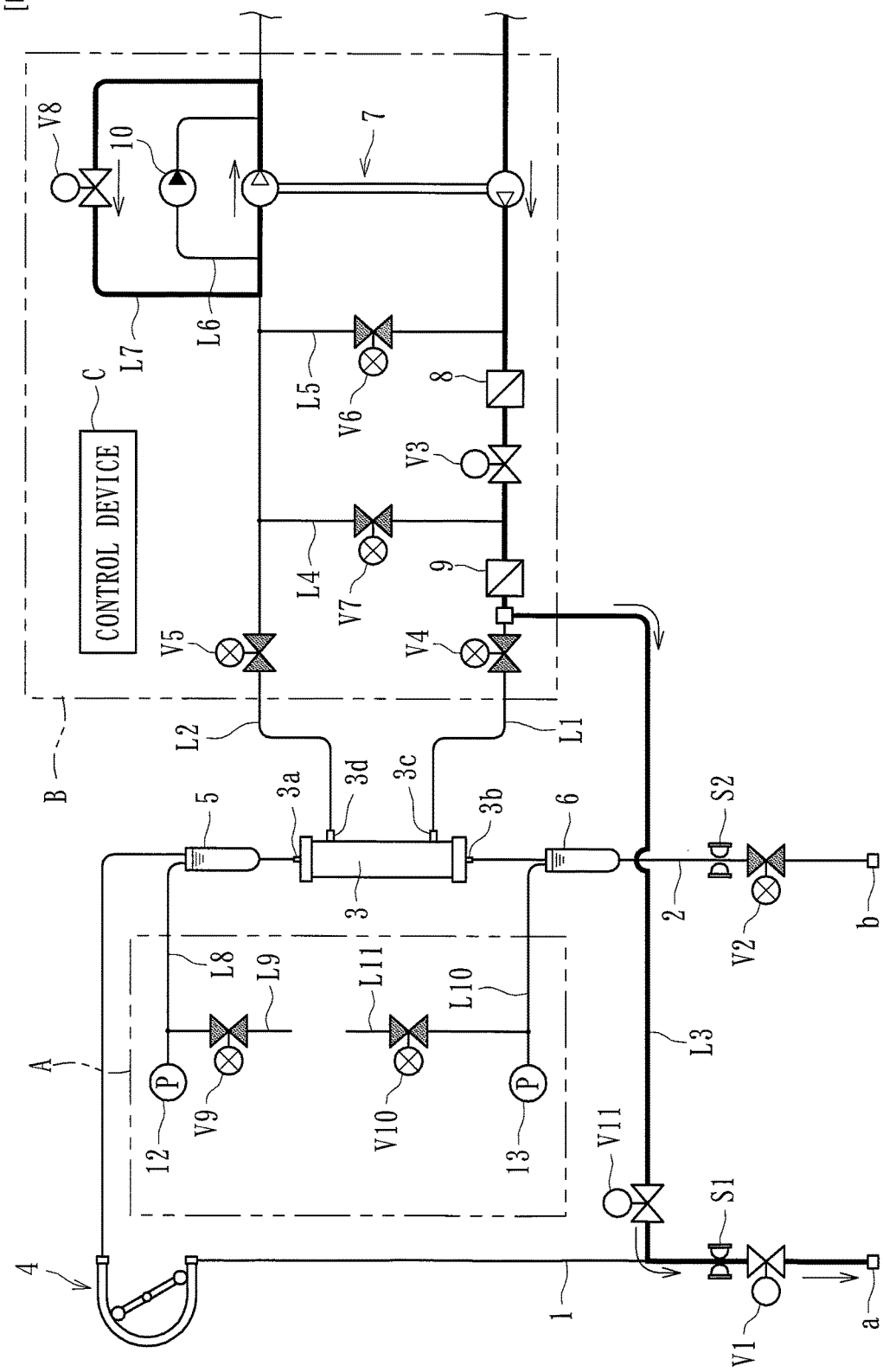

[Fig. 13]
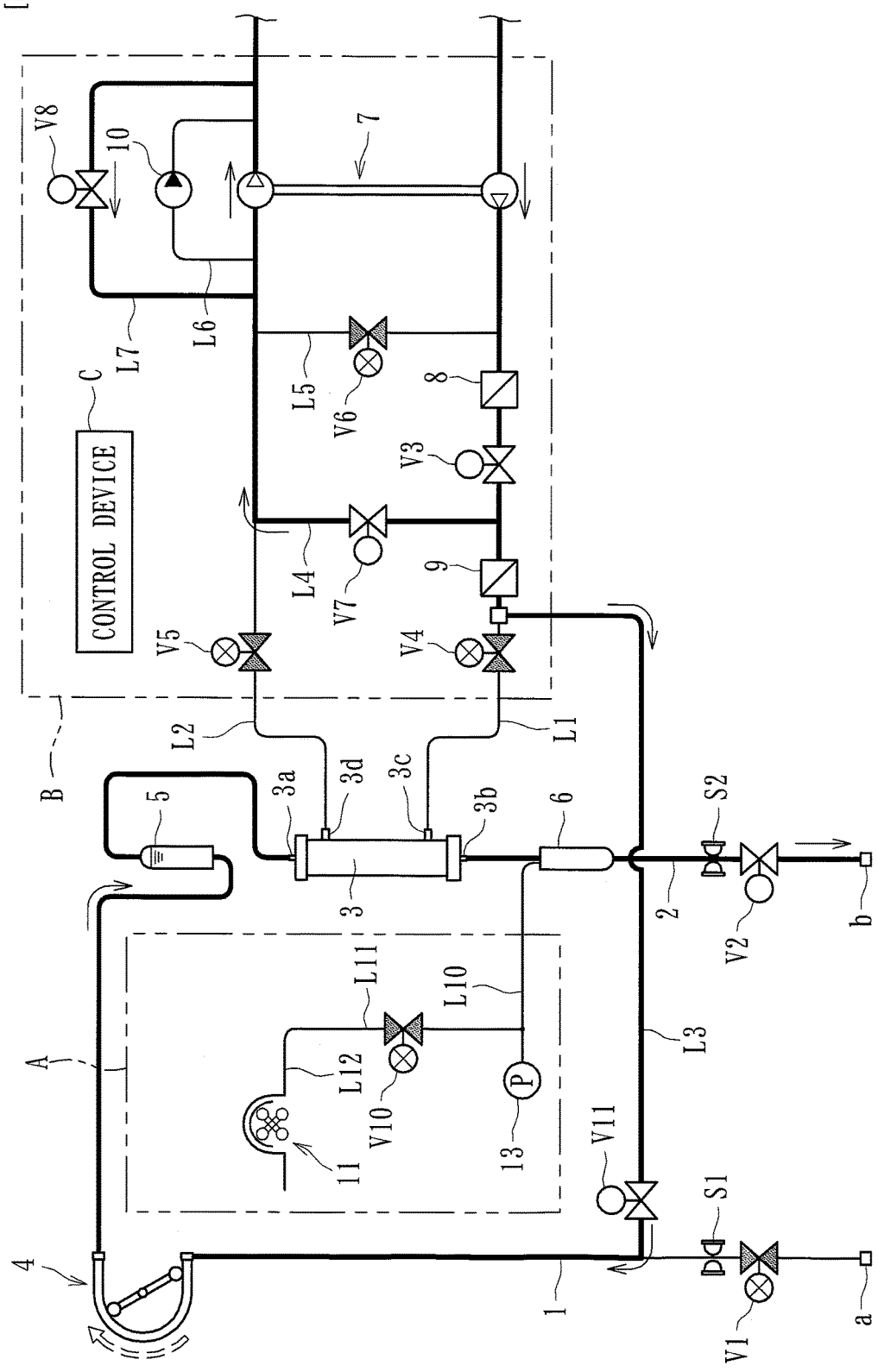

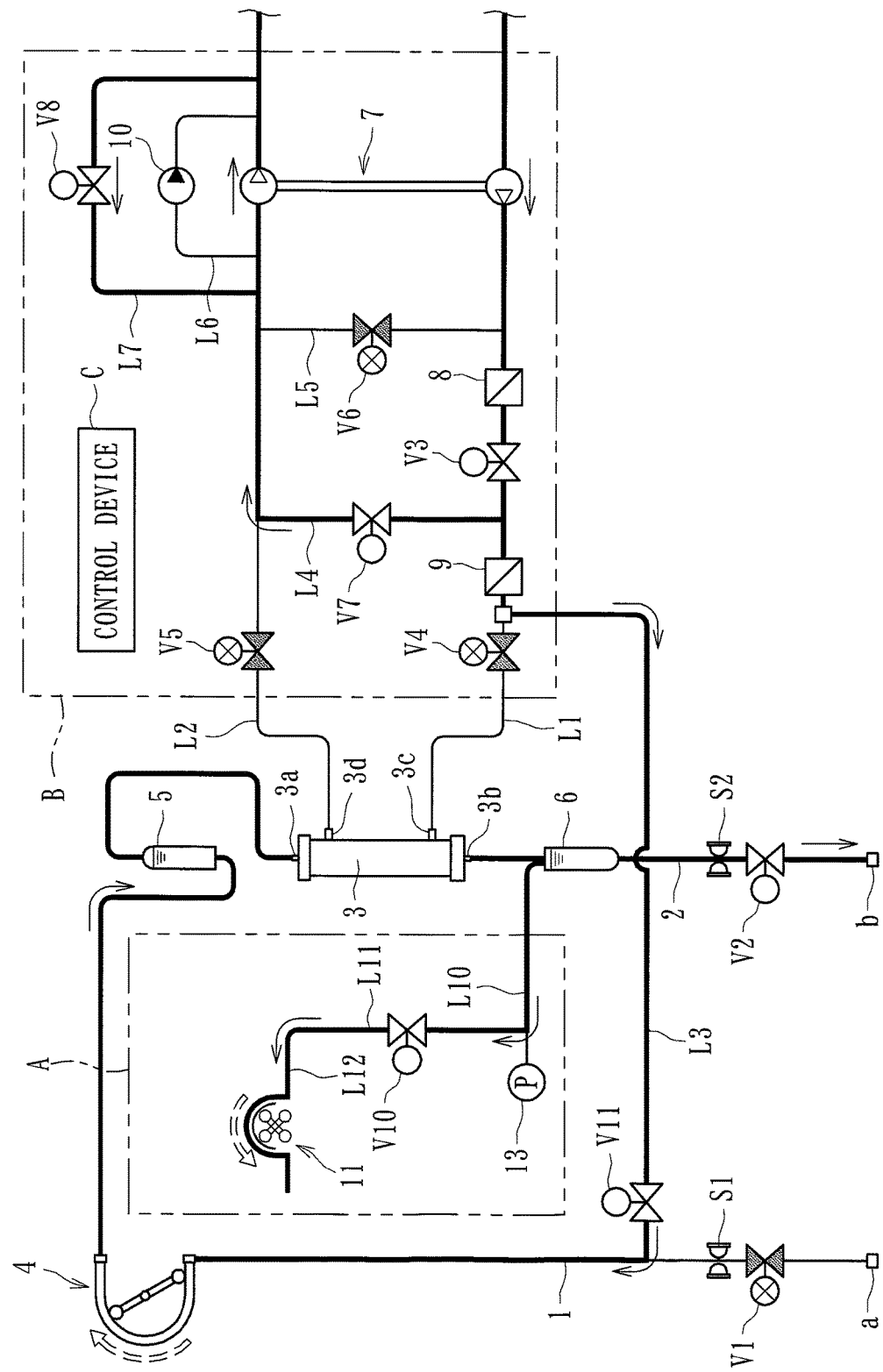
[Fig. 14]

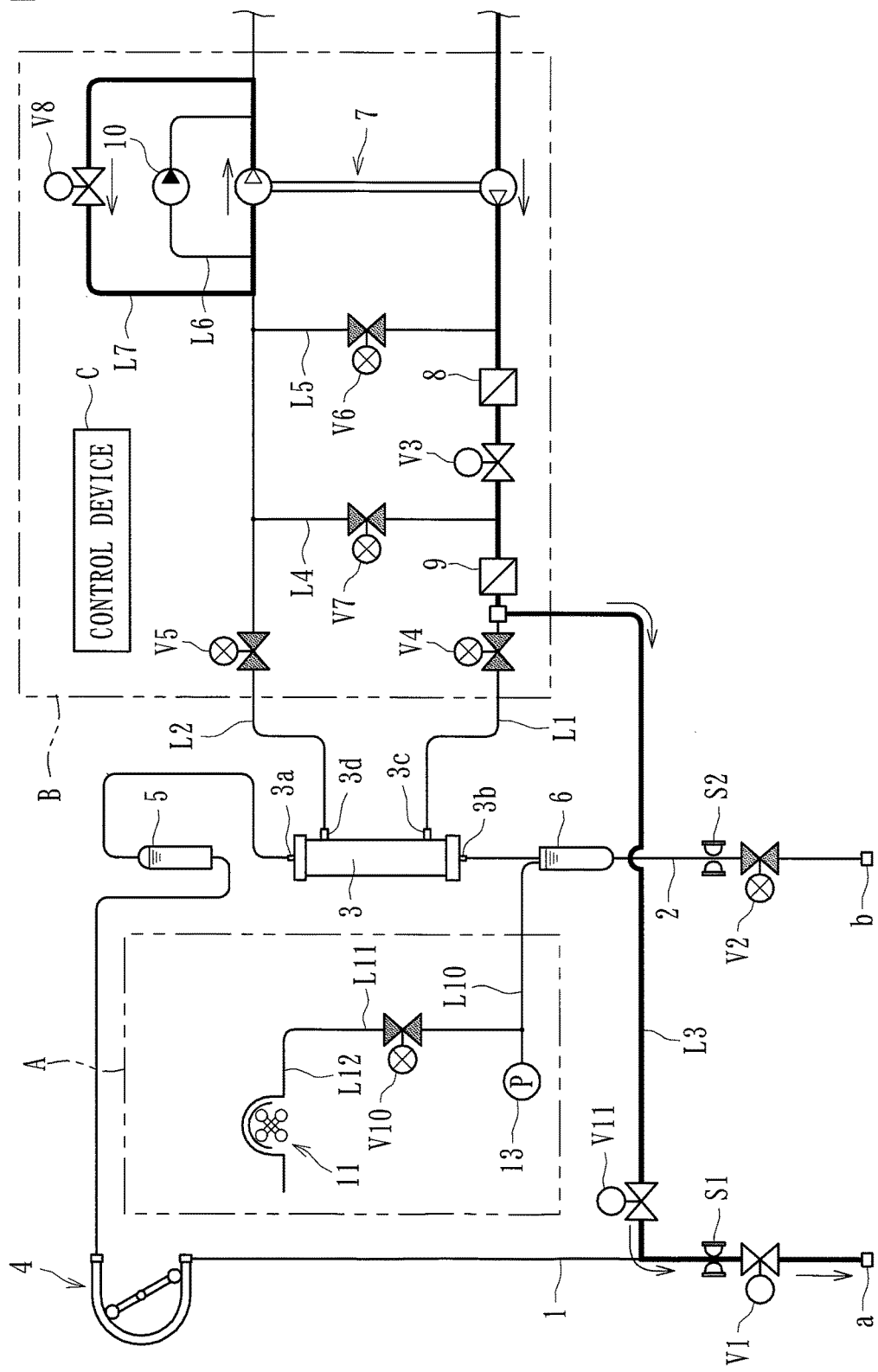
[Fig. 15]

[Fig. 16]
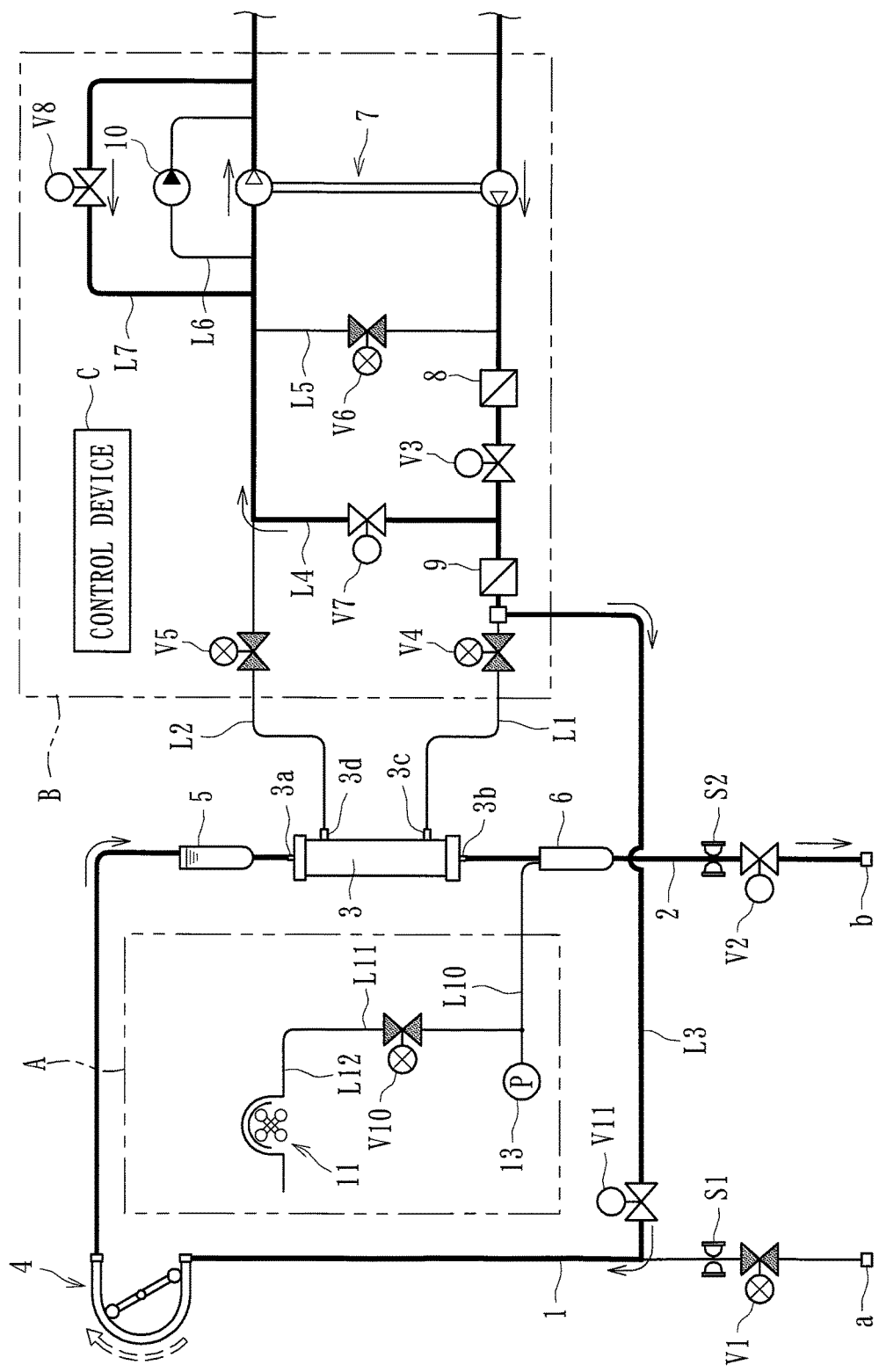

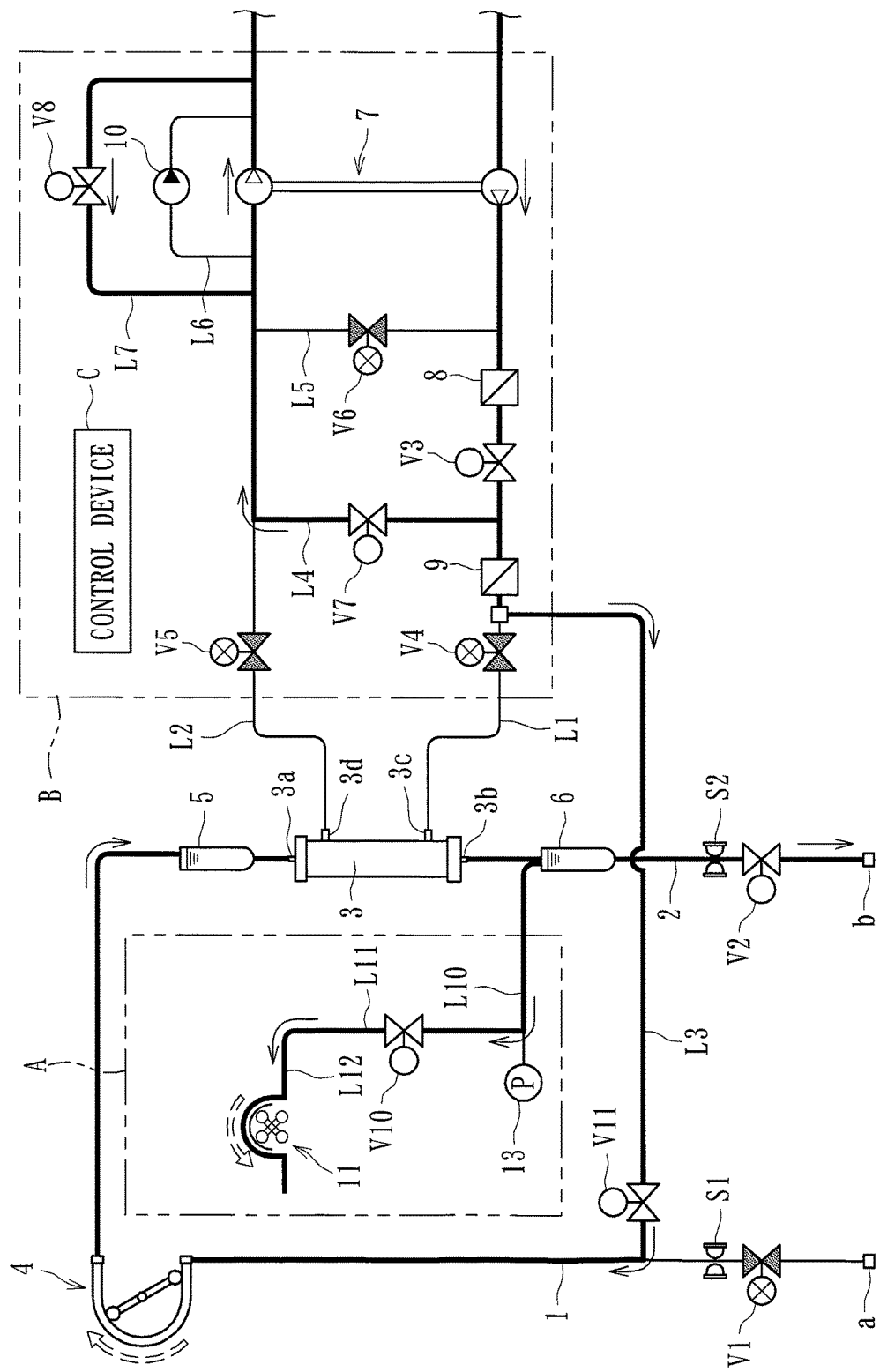
[Fig. 17]

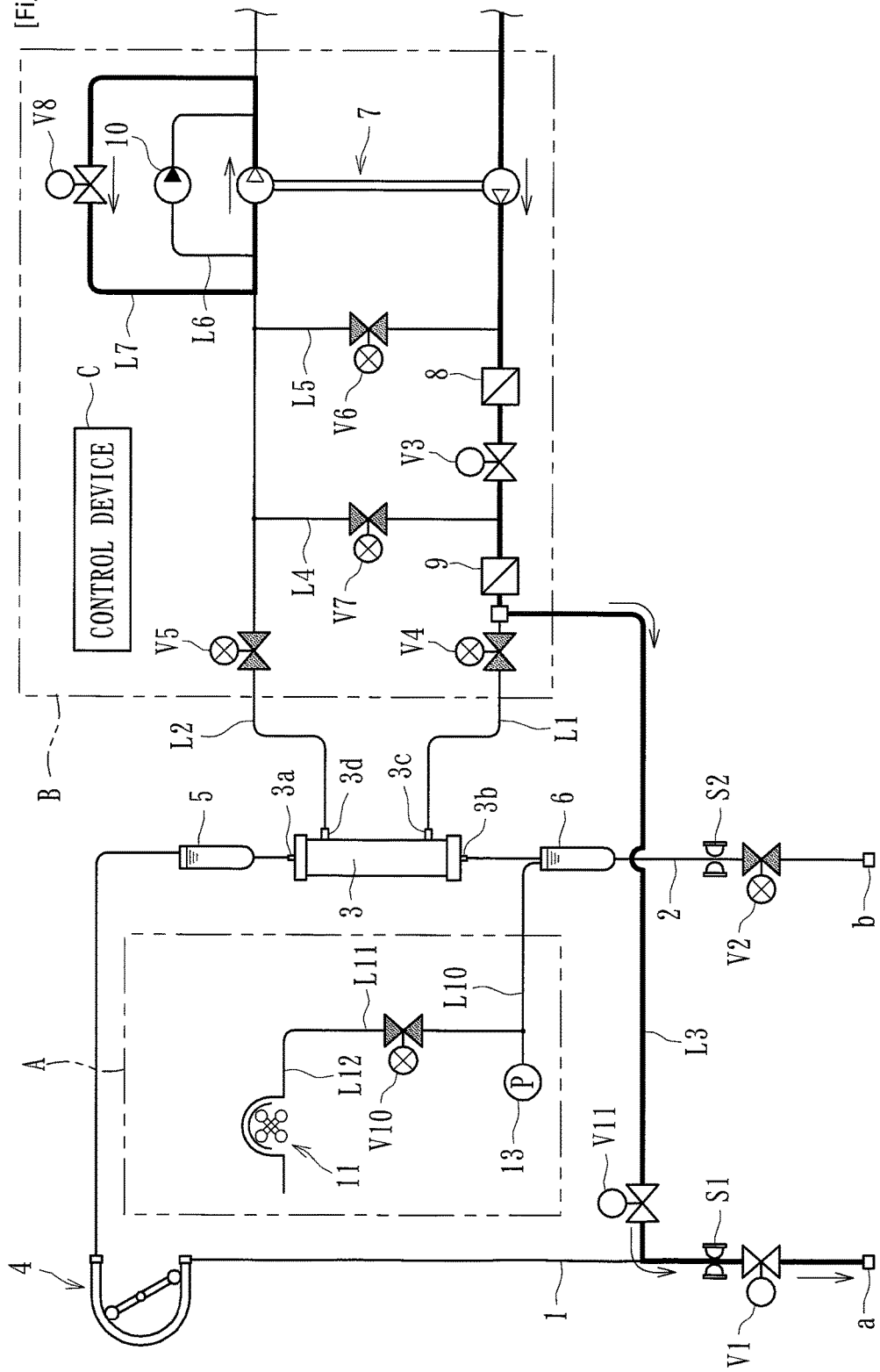
[Fig. 18]

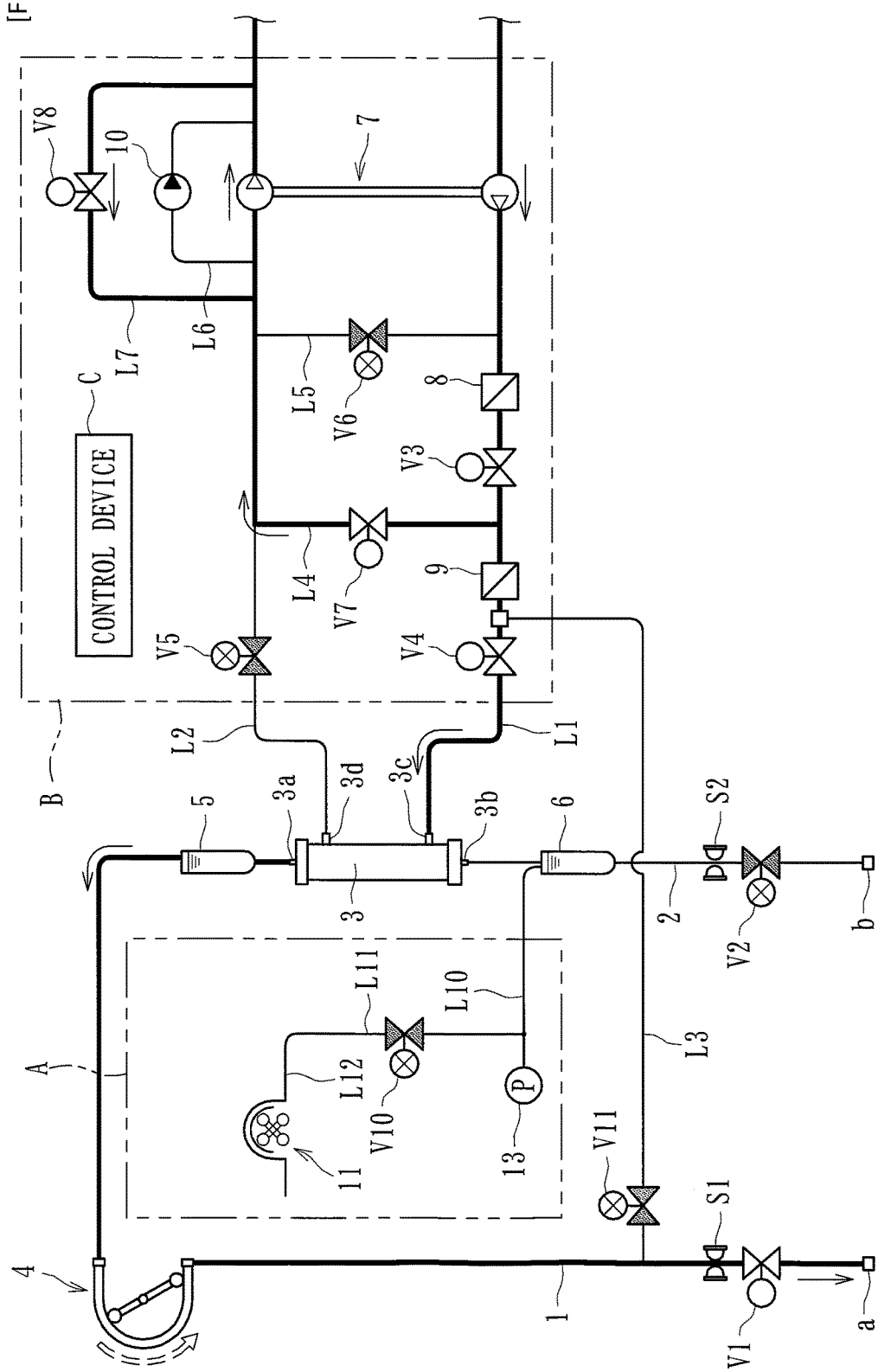
[Fig. 19]

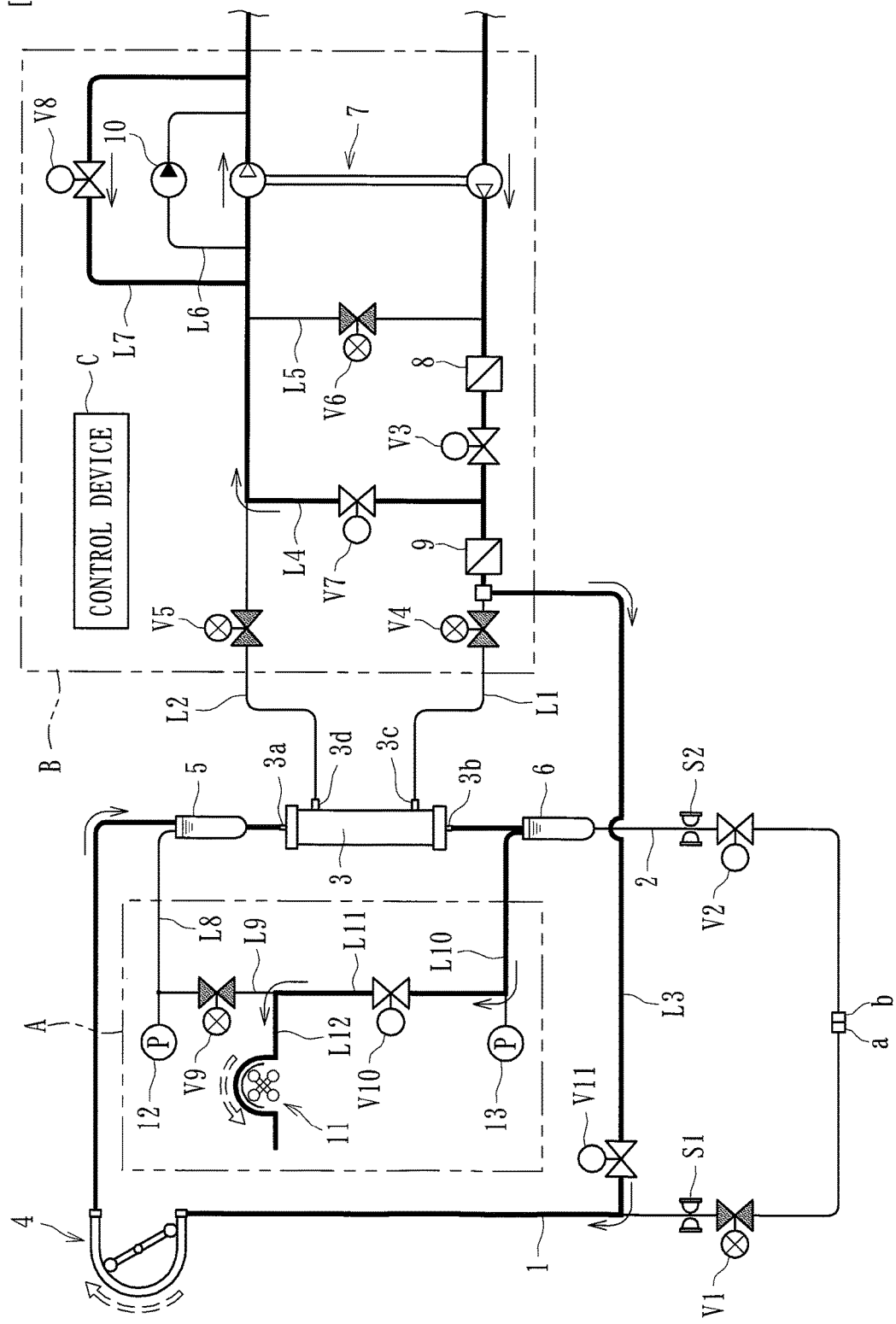
[Fig. 20]

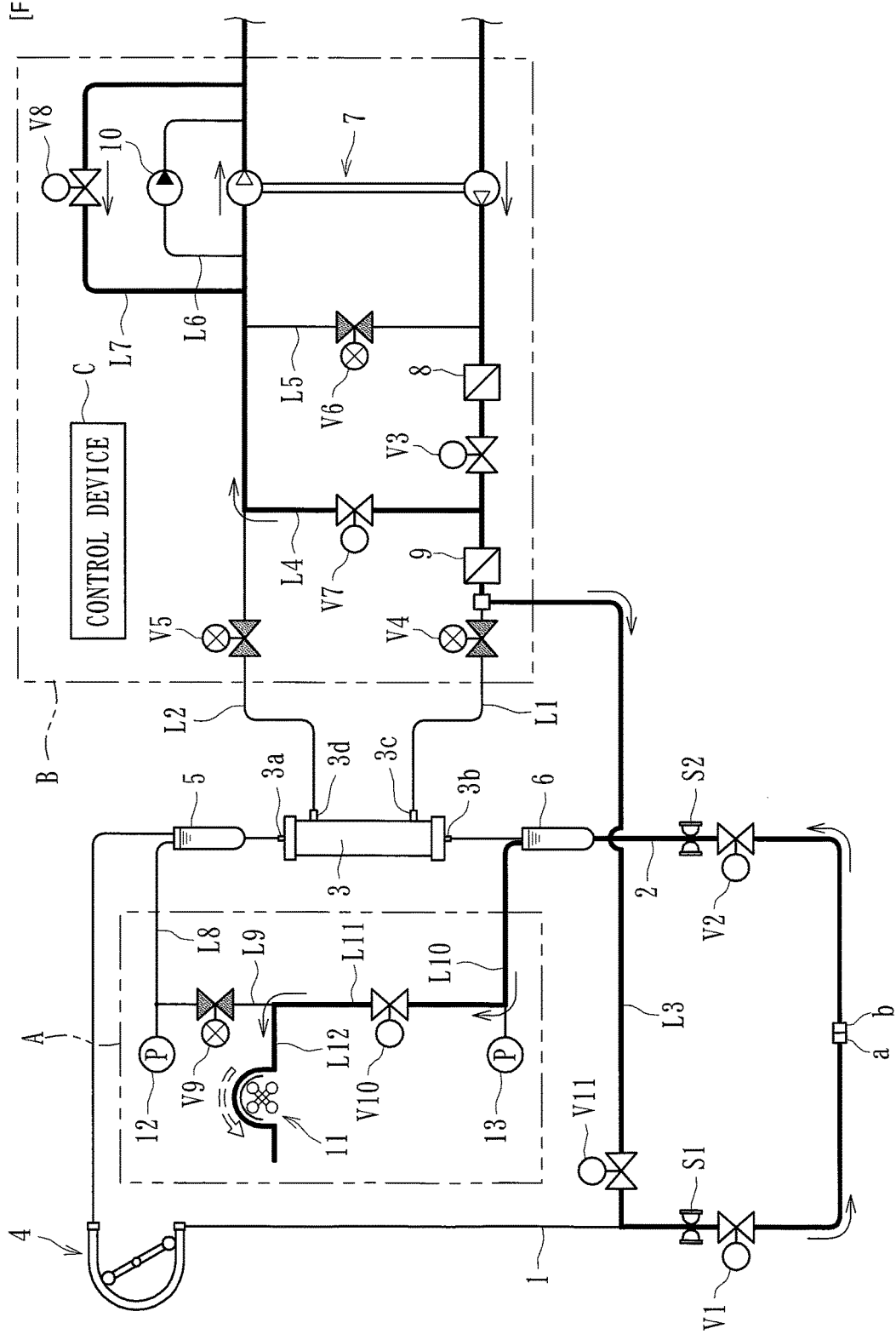

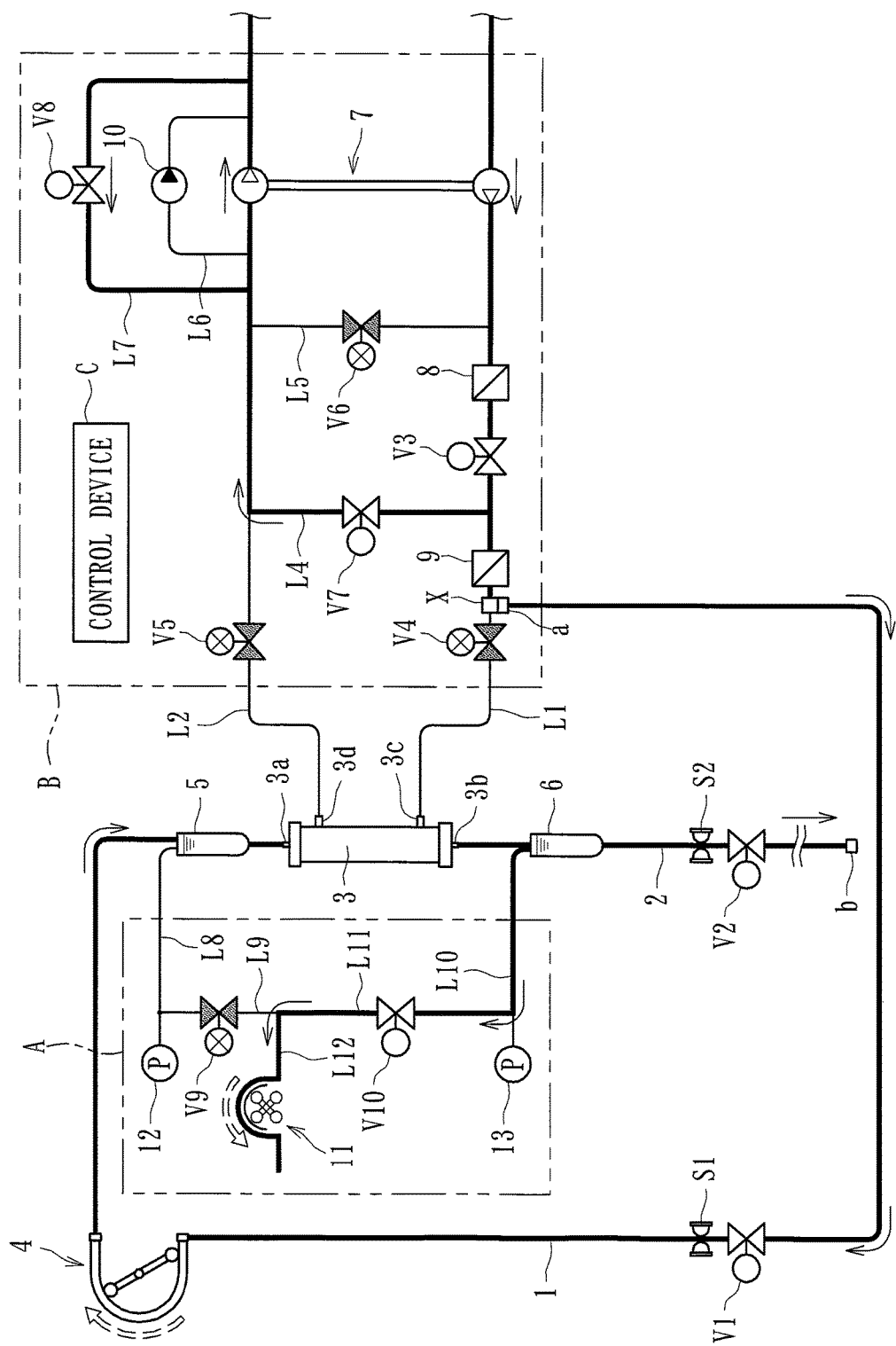
[Fig. 22]

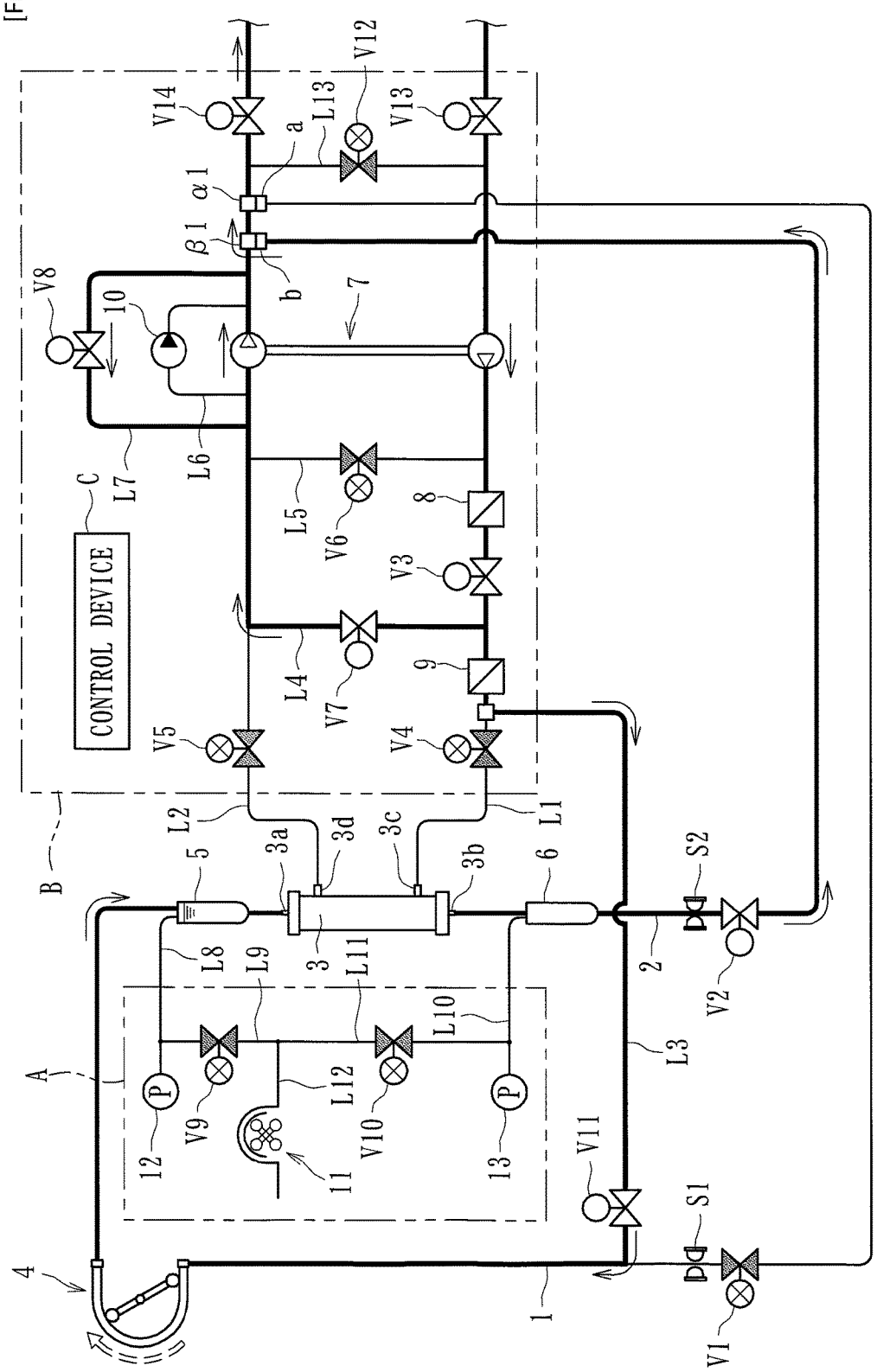

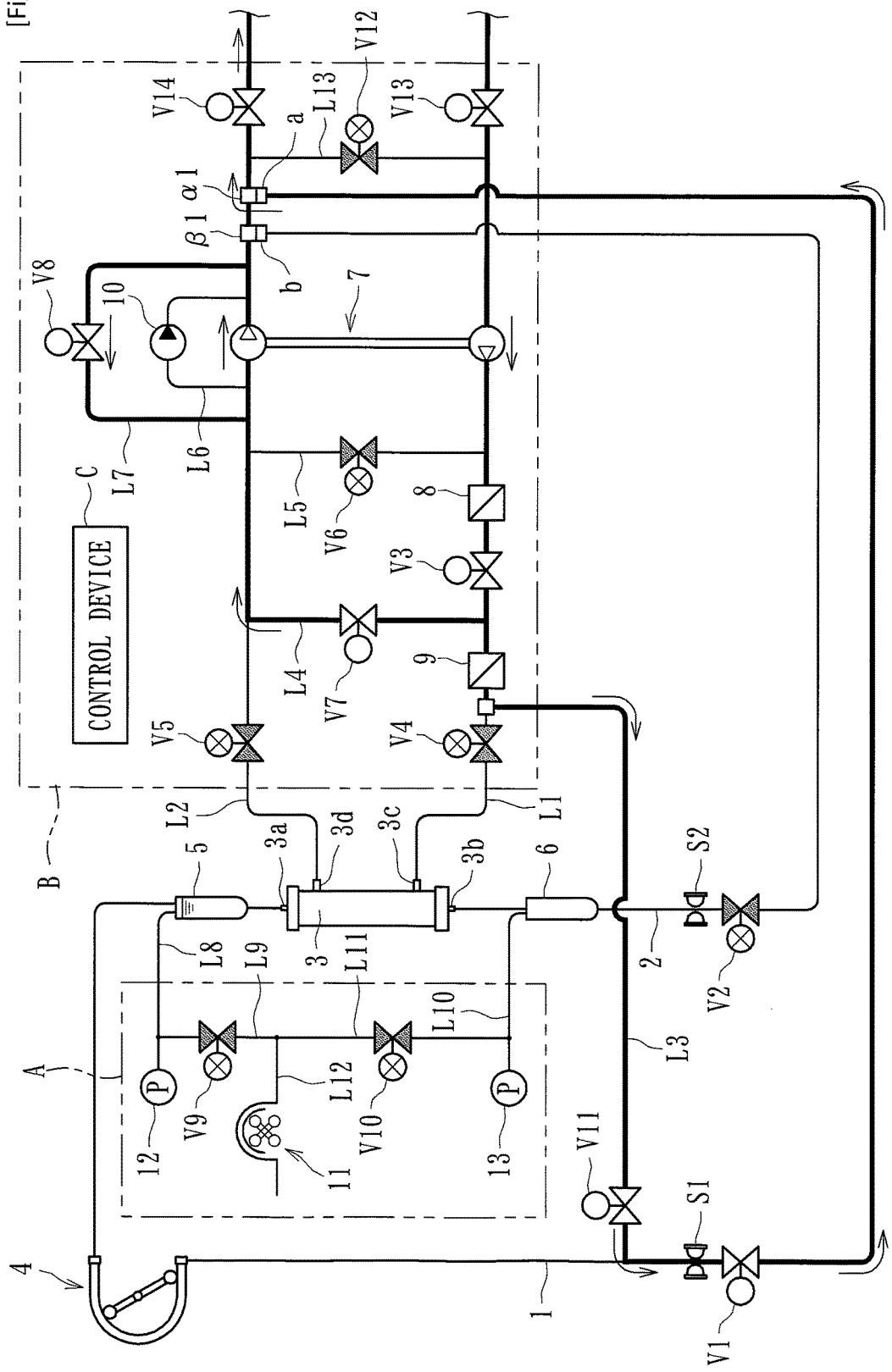

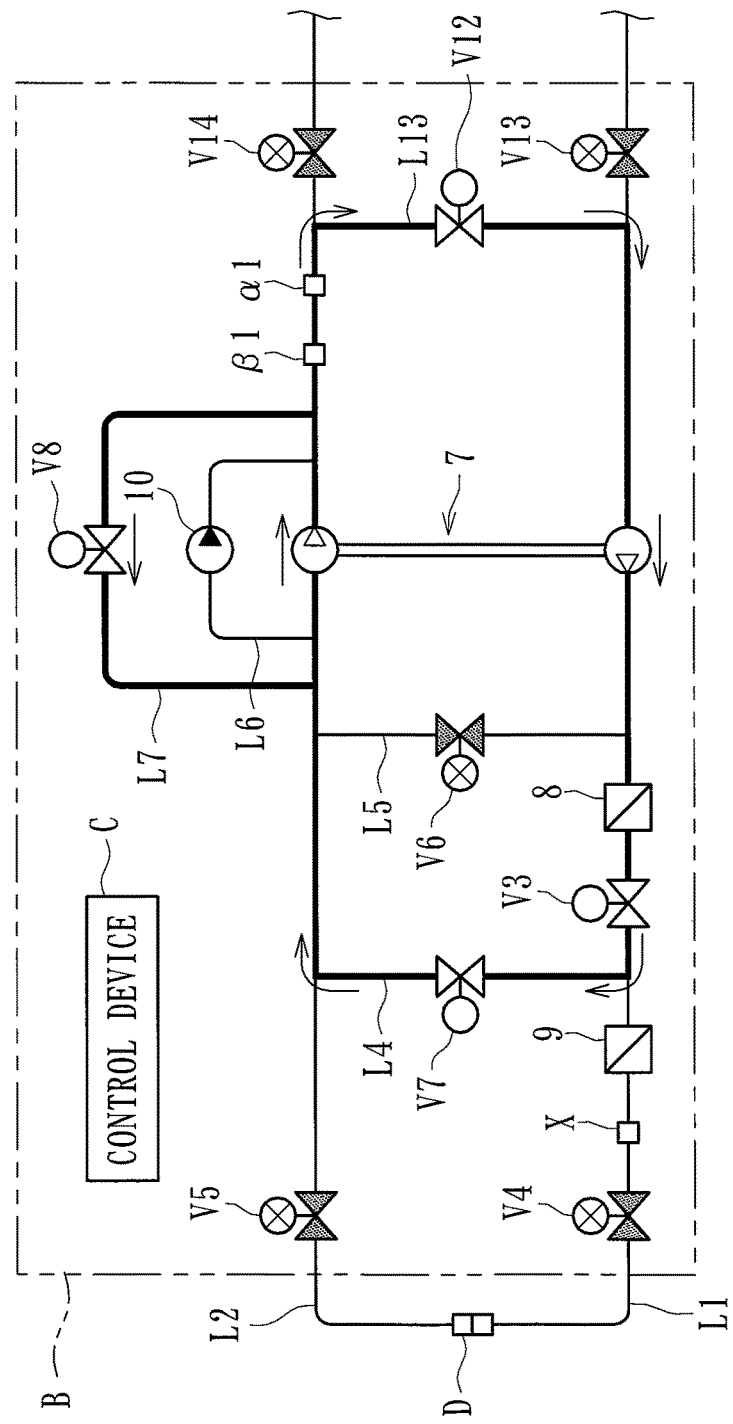
[Fig. 25]

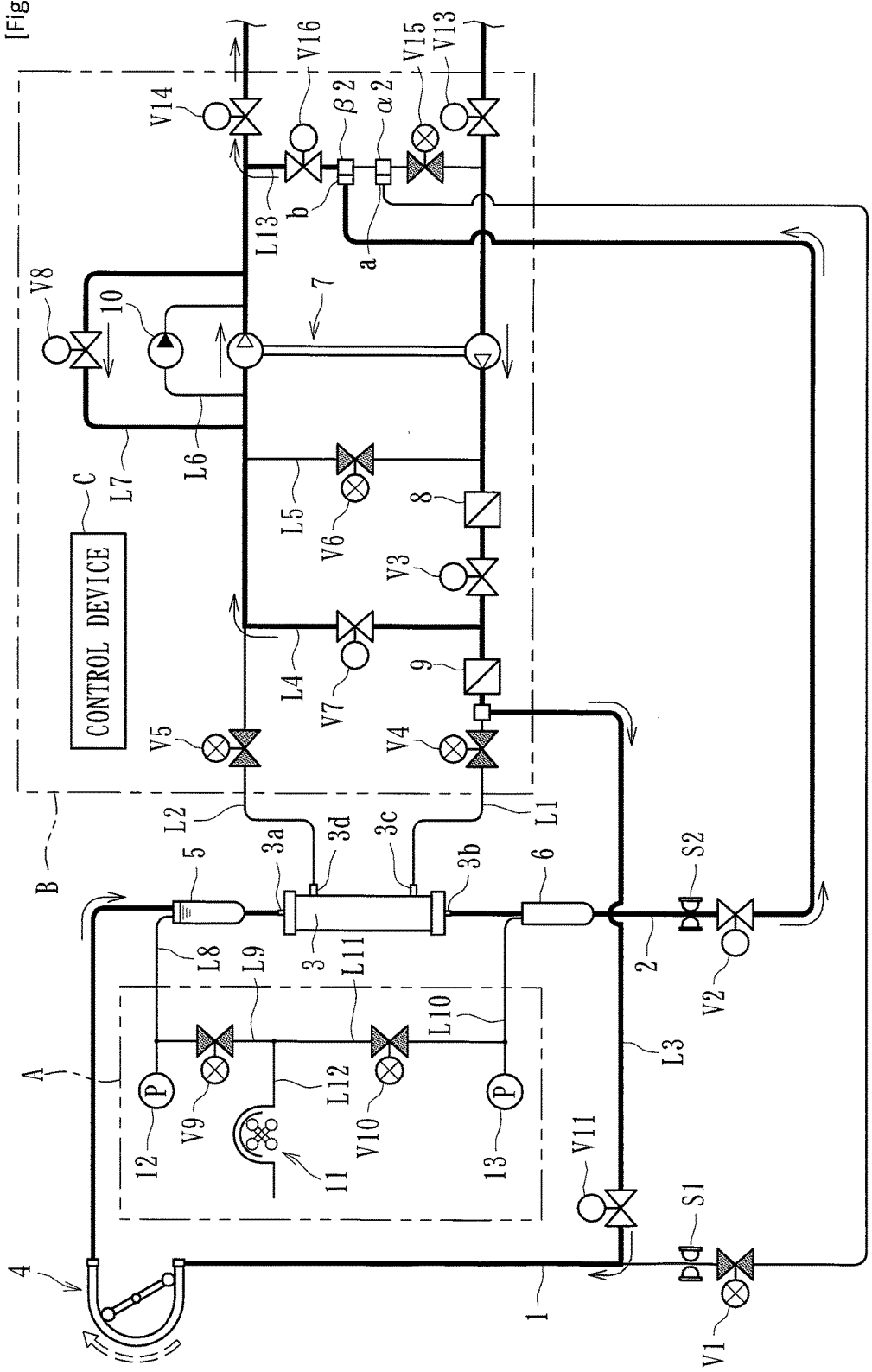
[Fig. 26]

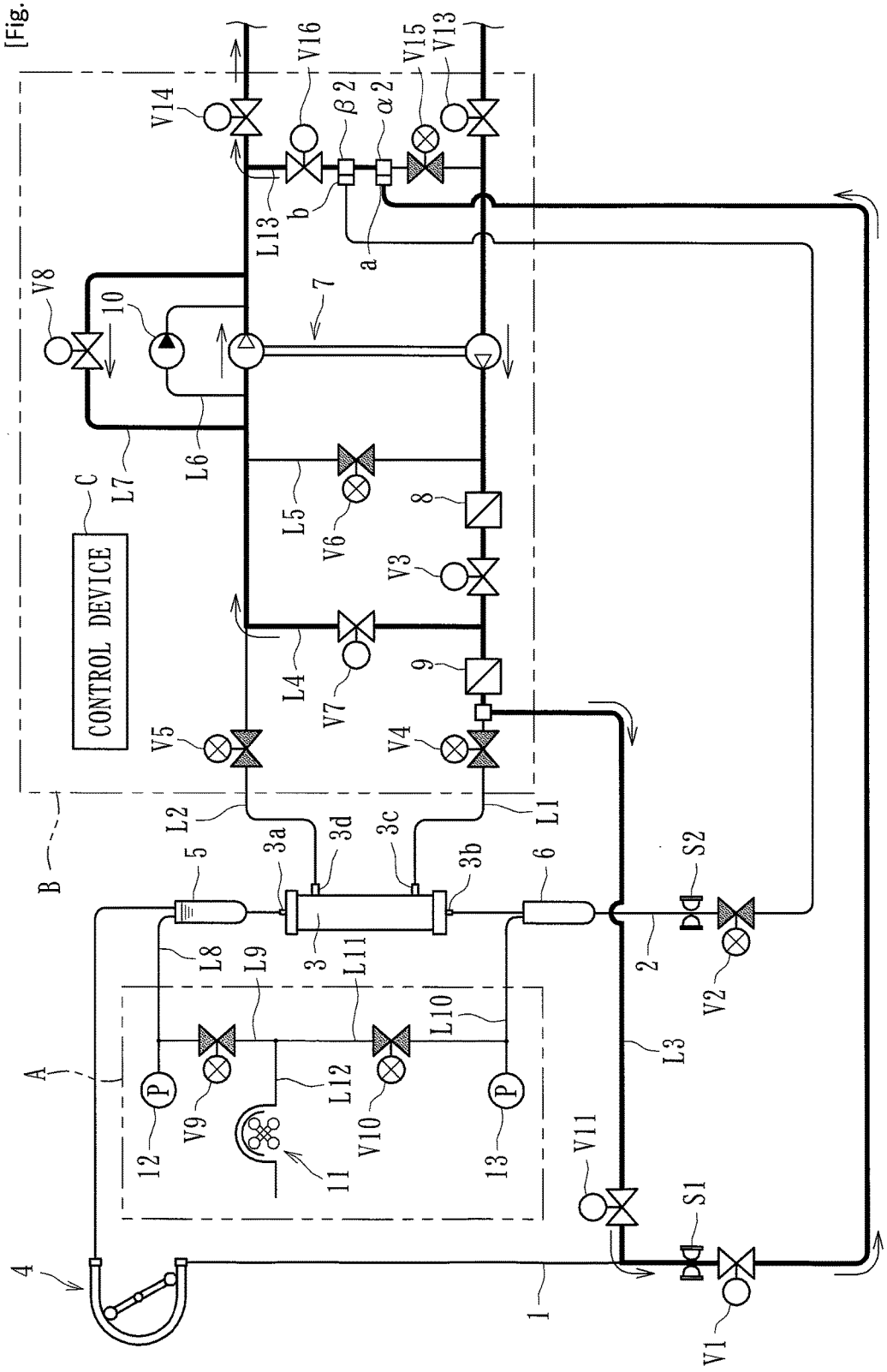

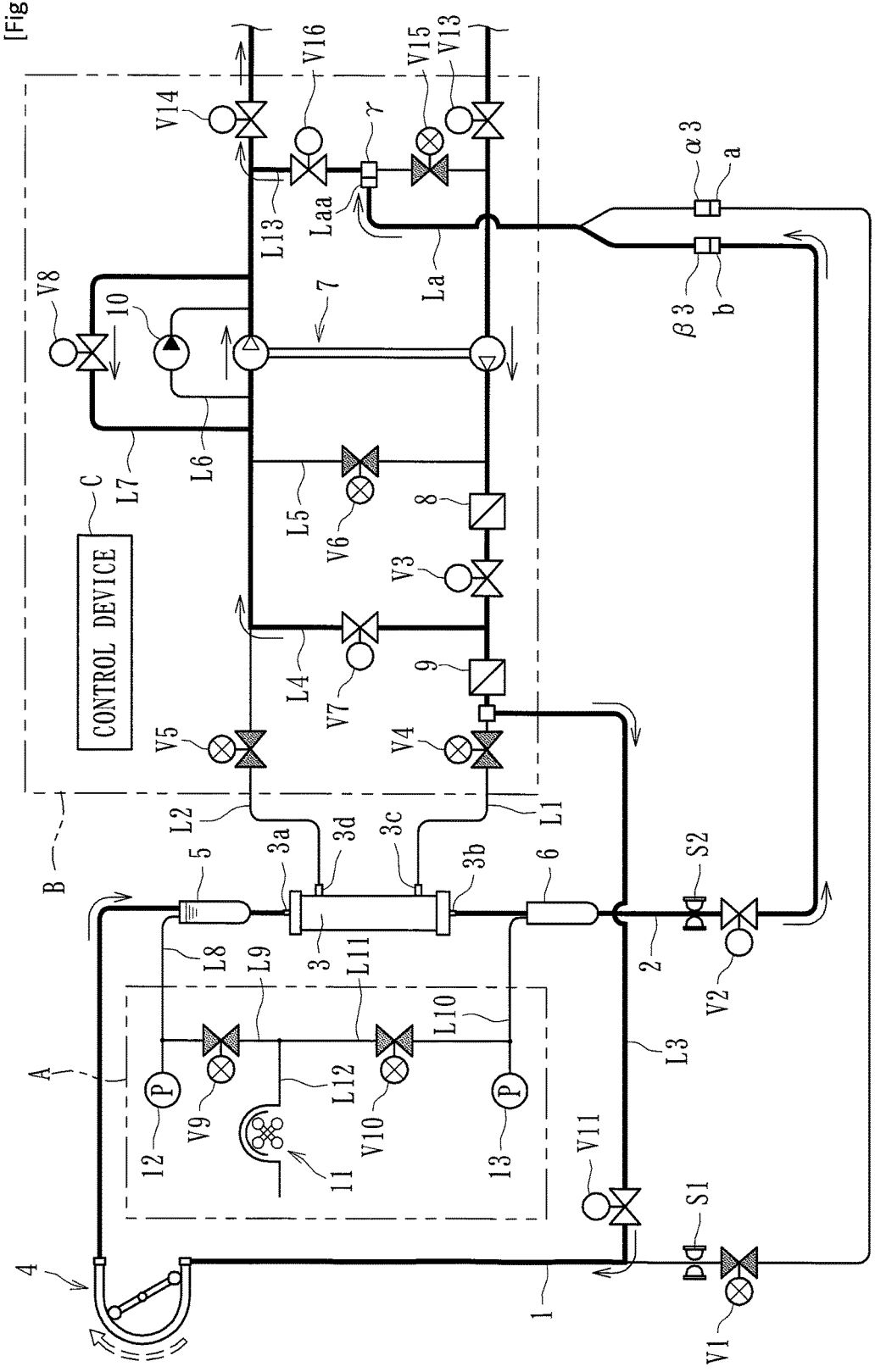
[Fig. 28]

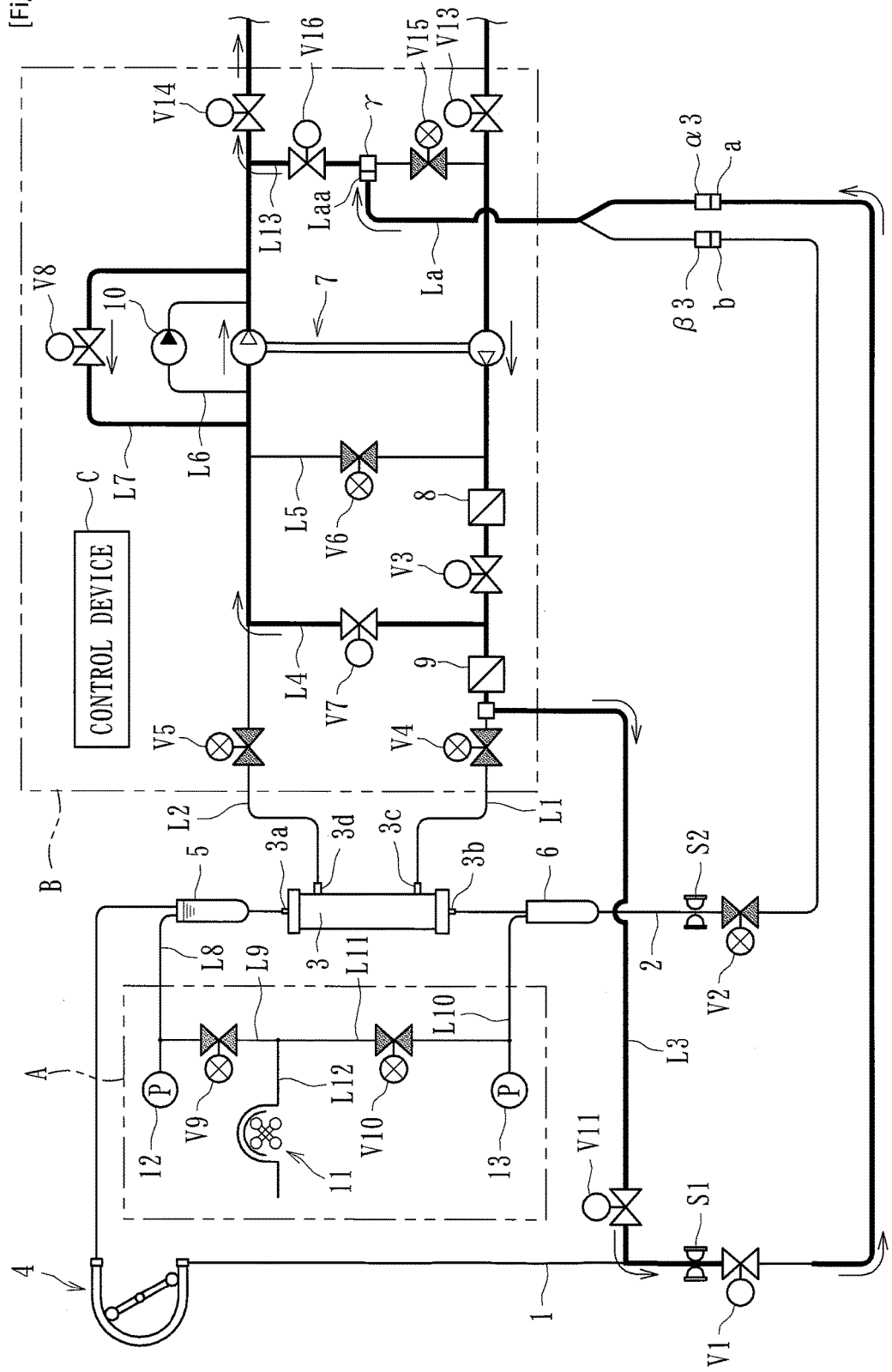

BLOOD PURIFICATION APPARATUS AND PRIMING METHOD FOR THE SAME

TECHNICAL FIELD

The present invention relates to a blood purification apparatus and a priming method for the same, which are used in order to extracorporeally circulate and purify blood of a patient during dialysis treatment using a dialyzer.

BACKGROUND ART

In general, during dialysis treatment, a blood circuit which extracorporeally circulates blood collected from a patient and returns the blood into an internal body of the patient is used. For example, the blood circuit is mainly configured to have an arterial blood circuit and a venous blood circuit which can be connected to a dialyzer (blood purification device) including a hollow fiber membrane. An arterial puncture needle and a venous puncture needle are attached to each distal end of the arterial blood circuit and the venous blood circuit. The respective needles are adapted to puncture the patient so as to perform extracorporeal circulation of the blood for the dialysis treatment.

Out of these, a peristaltic blood pump is arranged in the arterial blood circuit. In a state where the arterial puncture needle and the venous puncture needle puncture the patient, the blood pump is rotated. In this configuration, the blood collected from the internal body of the patient can be fed to the dialyzer side. Furthermore, an arterial air trap chamber and a venous air trap chamber are respectively connected to the arterial blood circuit and the venous blood circuit. The extracorporeally circulated blood is configured to return to the internal body of the patient after bubbles are removed.

Incidentally, in the related art, as disclosed in PTL 1, a configuration is adopted in which a priming solution supplying line for supplying a priming solution (physiological saline solution) during priming is connected via a T-shaped tube to an upstream side (that is, a side to which the arterial puncture needle is attached) from the blood pump in the arterial blood circuit, and in which the priming solution can flow into and can fill various configuration elements such as the blood circuits and the air trap chambers connected to the blood circuits during the priming prior to the dialysis treatment.

In particular, in the above-described blood purification apparatus in the related art, in order to automate the priming, an overflow line is extended from an upper portion of the venous air trap chamber, and a closed circuit is formed by connecting a distal end of the arterial blood circuit and a distal end of the venous blood circuit to each other during the priming. The priming solution supplied from the priming solution supplying line is circulated in the dosed circuit, and is discharged through the overflow line. In this manner, filling with priming solution can be performed automatically.

CITATION LIST

Patent Literature

PTL 1: Japanese Unexamined Patent Application Publication No. 2010-273693

Technical Problem

However, in the above-described blood purification apparatus in the related art, it is necessary to prepare dedicated components such as connection instruments for connecting the overflow line which is limitedly used only for the priming, the distal end of the arterial blood circuit, and the distal end of the venous blood circuit. Consequently, there is a disadvantage in that the manufacturing cost for the blood circuit increases at least to that extent that the dedicated components are provided. However, since the blood circuit is generally a throwaway good (disposable good) after each treatment, it is necessary to prepare the dedicated components for each treatment. Consequently, there is a problem in that not only the manufacturing cost increases, but also the inventory management for the dedicated components becomes cumbersome. Therefore, the applicant has focused on a liquid level adjustment device which can adjust a liquid level of the air trap chamber during treatment, and has closely studied that the dedicated components for the priming are reduced or dispensed with by performing the priming of the blood circuit using the liquid level adjustment device.

The present invention is made in view of the above-described circumstances, and aims to provide a blood purification apparatus and a priming method for the same, which can reduce or dispense with dedicated components used for automated priming and which can reduce manufacturing costs of a blood circuit while achieving the automated priming.

SUMMARY

According to the teachings herein, there is provided a blood purification apparatus including a blood circuit that includes an arterial blood circuit and a venous blood circuit, and that extracorporeally circulates blood of a patient from a distal end of the arterial blood circuit to a distal end of the venous blood circuit, a blood purification device that is interposed between the arterial blood circuit and the venous blood circuit in the blood circuit, and that can purify the blood flowing in the blood circuit, a blood pump that is arranged in the arterial blood circuit, a venous air trap chamber that is connected to the venous blood circuit, a liquid level adjustment device that is connected to the venous air trap chamber, and that can optionally introduce or discharge air into or from an upper portion of the venous air trap chamber, a control device that can adjust a liquid level formed inside the venous air trap chamber to have the height at any desired position by operating the liquid level adjustment device, and a priming solution supplying line that can supply a priming solution to the arterial blood circuit and the venous blood circuit during priming. During the priming, the control device can fill the arterial blood circuit and the venous blood circuit with the priming solution supplied from the priming solution supplying line by operating the liquid level adjustment device at any desired timing.

According to the teachings herein, in the blood purification apparatus as taught herein, during the priming, the distal end of the arterial blood circuit and the distal end of the venous blood circuit are respectively brought into a released state, and the priming solution supplied from the priming solution supplying line can be discharged from the distal end of the arterial blood circuit and the distal end of the venous blood circuit.

According to the teachings herein, the blood purification apparatus as is disclosed herein further includes a dialysate introduction line that introduces a dialysate to the blood purification device and a dialysate discharge line that discharges the dialysate from the blood purification device. During the priming, the distal end of the arterial blood circuit and the distal end of the venous blood circuit are respectively connected to the dialysate discharge line or a connection line which connects the dialysate introduction line and the dialysate discharge line to each other, and the priming solution supplied from the priming solution supplying line can be discharged from the distal end of the arterial blood circuit and the distal end of the venous blood circuit via the dialysate discharge line.

According to the teachings herein, the blood purification apparatus as is disclosed herein, the dialysate discharge line includes a pump which discharges the dialysate from the blood purification device to the dialysate discharge line. During the priming, the distal end of the arterial blood circuit and the distal end of the venous blood circuit are connected to the dialysate discharge line or to a downstream side from the pump in the connection line.

According to the teachings herein, the blood purification apparatus as is disclosed herein further includes a connection device that includes a first connection portion and a second connection portion which can be respectively connected to the distal end of the arterial blood circuit and the distal end of the venous blood circuit, and a third connection portion which can be connected to the dialysate discharge line or the connection line. During the priming, the priming solution supplied from the priming solution supplying line can be discharged from the distal end of the arterial blood circuit and the distal end of the venous blood circuit to the dialysate discharge line or the connection line via the connection device.

According to the teachings herein, in the blood purification apparatus disclosed as is disclosed herein, the liquid level adjustment device includes a liquid level adjustment pump which can perform normal rotation and reverse rotation. During the priming, the control device can introduce or discharge air to or from an upper portion of the venous air trap chamber by rotating the liquid level adjustment pump at any desired timing.

According to the teachings herein, in the blood purification apparatus disclosed as is disclosed herein, the arterial air trap chamber is connected to the arterial blood circuit, and the liquid level adjustment device is connected to each of the arterial air trap chamber and the venous air trap chamber, and the control device can adjust each liquid level formed inside the arterial air trap chamber and the venous air trap chamber to have the height at any desired position.

According to the teachings herein, the blood purification apparatus disclosed as is disclosed herein, further includes a dialysate introduction line that introduces a dialysate to the blood purification device and a dialysate discharge line that discharges the dialysate from the blood purification device. The priming solution supplying line is configured so that one end is connected to the dialysate introduction line and the other end is connected to a predetermined portion of the blood circuit, and can supply the dialysate of the dialysate introduction line to the arterial blood circuit and the venous blood circuit.

According to the teachings herein, in the blood purification apparatus disclosed as is disclosed herein, the liquid level adjustment device can discharge the priming solution from the venous air trap chamber.

According to the teachings herein, there is provided a priming method for a blood purification apparatus that includes a blood circuit which includes an arterial blood circuit and a venous blood circuit, and which extracorporeally circulates blood of a patient from a distal end of the arterial blood circuit to a distal end of the venous blood circuit, a blood purification device which is interposed between the arterial blood circuit and the venous blood circuit in the blood circuit, and which can purify the blood flowing in the blood circuit, a blood pump which is arranged in the arterial blood circuit, a venous air trap chamber which is connected to the venous blood circuit, a liquid level adjustment device which is connected to the venous air trap chamber, and which can optionally introduce or discharge air into or from an upper portion of the venous air trap chamber, and a priming solution supplying line which can supply a priming solution to the arterial blood circuit and the venous blood circuit during priming, and that can adjust a liquid level formed inside the venous air trap chamber to have the height at any desired position by operating the liquid level adjustment device. During the priming, the arterial blood circuit and the venous blood circuit are filled with the priming solution supplied from the priming solution supplying line by operating the liquid level adjustment device at any desired timing.

According to the teachings herein, in the priming method for a blood purification apparatus disclosed herein, during the priming, the distal end of the arterial blood circuit and the distal end of the venous blood circuit are respectively brought into a released state, and the priming solution supplied from the priming solution supplying line is discharged from the distal end of the arterial blood circuit and the distal end of the venous blood circuit.

According to the teachings herein, in the priming method for a blood purification apparatus disclosed herein, the blood purification apparatus further includes a dialysate introduction line that introduces a dialysate to the blood purification device and a dialysate discharge line that discharges the dialysate from the blood purification device. During the priming, the distal end of the arterial blood circuit and the distal end of the venous blood circuit are respectively connected to the dialysate discharge line or a connection line which connects the dialysate introduction line and the dialysate discharge line to each other, and the priming solution supplied from the priming solution supplying line is discharged from the distal end of the arterial blood circuit and the distal end of the venous blood circuit via the dialysate discharge line.

According to the teachings herein, in the priming method for a blood purification apparatus disclosed herein, the dialysate discharge line includes a pump which discharges the dialysate from the blood purification device to the dialysate discharge line, and during the priming, the distal end of the arterial blood circuit and the distal end of the venous blood circuit are connected to the dialysate discharge line or to a downstream side from the pump in the connection line.

According to the teachings herein, in the priming method for a blood purification apparatus disclosed herein, the blood purification apparatus further includes a connection device that includes a first connection portion and a second connection portion which can be respectively connected to the distal end of the arterial blood circuit and the distal end of the venous blood circuit, and a third connection portion which can be connected to the dialysate discharge line or the connection line, and during the priming, the priming solution supplied from the priming solution supplying line can be discharged from the distal end of the arterial blood circuit and the distal end of the venous blood circuit to the dialysate discharge line or the connection line via the connection device.

According to the teachings herein, in the priming method for a blood purification apparatus as is disclosed herein, the liquid level adjustment device includes a liquid level adjustment pump which can perform normal rotation and reverse rotation, and during the priming, the control device can introduce or discharge air to or from an upper portion of the venous air trap chamber by rotating the liquid level adjustment pump at any desired timing.

According to the teachings herein, in the priming method for a blood purification apparatus as is disclosed herein, the arterial air trap chamber is connected to the arterial blood circuit, and the liquid level adjustment device is connected to each of the arterial air trap chamber and the venous air trap chamber, and the control device can adjust each liquid level formed inside the arterial air trap chamber and the venous air trap chamber to have the height at any desired position.

According to the teachings herein, in the priming method for a blood purification apparatus as is disclosed herein, the blood purification apparatus further includes a dialysate introduction line that introduces a dialysate to the blood purification device and a dialysate discharge line that discharges the dialysate from the blood purification device. The priming solution supplying line is configured so that one end is connected to the dialysate introduction line and the other end is connected to a predetermined portion of the blood circuit, and supplies the dialysate of the dialysate introduction line to the arterial blood circuit and the venous blood circuit.

According to the teachings herein, in the priming method for a blood purification apparatus as is disclosed herein, the liquid level adjustment device can discharge the priming solution from the venous air trap chamber.

According to the teachings herein, during the priming, the arterial blood circuit and the venous blood circuit are filled with the priming solution supplied from the priming solution supplying line by operating the liquid level adjustment device at any desired timing. Accordingly, dedicated components used for automated priming can be reduced or dispensed with. Therefore, it is possible to reduce manufacturing costs of the blood circuit while achieving the automated priming.

According to the teachings herein, during the priming, the distal end of the arterial blood circuit and the distal end of the venous blood circuit are respectively brought into the released state, and the priming solution supplied from the priming solution supplying line is discharged from the distal end of the arterial blood circuit and the distal end of the venous blood circuit. Accordingly, within the dedicated components used for the automated priming, it is possible to dispense with at least an overflow line and a connection instrument for connecting the distal end of the arterial blood circuit and the distal end of the venous blood circuit to each other.

According to the teachings herein, during the priming, the distal end of the arterial blood circuit and the distal end of the venous blood circuit are respectively connected to the dialysate discharge line or the connection line which connects the dialysate introduction line and the dialysate discharge line to each other. The priming solution supplied from the priming solution supplying line can be discharged from the distal end of the arterial blood circuit and the distal end of the venous blood circuit via the dialysate discharge line. Accordingly, the priming solution used during the priming can be discharged using the dialysate discharge line. Therefore, the priming solution can be easily collected.

According to the teachings herein, the dialysate discharge line includes the pump which discharges the dialysate from the blood purification device to the dialysate discharge line. During the priming, the distal end of the arterial blood circuit and the distal end of the venous blood circuit are connected to the dialysate discharge line or to the downstream side from the pump in the connection line. Accordingly, it is possible to reliably avoid a case where the priming solution discharged from the distal end of the arterial blood circuit and the distal end of the venous blood circuit unintentionally reaches the blood purification device.

According to the teachings herein, there is provided the connection device including the first connection portion and the second connection portion which can be respectively connected to the distal end of the arterial blood circuit and the distal end of the venous blood circuit, and the third connection portion which can be connected to the dialysate discharge line or the connection line. During the priming, the priming solution supplied from the priming solution supplying line is discharged from the distal end of the arterial blood circuit and the distal end of the venous blood circuit to the dialysate discharge line or the connection line via the connection device. Accordingly, it is possible to avoid a case where the distal end of the arterial blood circuit and the distal end of the venous blood circuit unintentionally come into contact with a main body of the apparatus including the dialysate discharge line. Therefore, the main body of the apparatus can be maintained cleanly.

According to the teachings herein, the liquid level adjustment device includes the liquid level adjustment pump which can perform normal rotation and reverse rotation. During the priming, the control device can introduce or discharge the air to or from the upper portion of the venous air trap chamber by rotating the liquid level adjustment pump at any desired timing. Accordingly, an optimal amount of air can be introduced to or discharged from the venous air trap chamber during treatment and during the priming.

According to the teachings herein, the arterial air trap chamber is connected to the arterial blood circuit, and the liquid level adjustment device is connected to each of the arterial air trap chamber and the venous air trap chamber. The control device can adjust each liquid level formed inside the arterial air trap chamber and the venous air trap chamber to have the height at any desired position. Accordingly, each liquid level in the arterial air trap chamber and the venous air trap chamber can be adjusted to have the optimal height during the treatment and during the priming.

According to the teachings herein, the priming solution supplying line is configured so that one end is connected to the dialysate introduction line and the other end is connected to a predetermined portion of the blood circuit, and supplies the dialysate of the dialysate introduction line to the arterial blood circuit and the venous blood circuit. Accordingly, as compared to a case where a physiological saline solution is supplied as the priming solution, automated priming can be more smoothly achieved.

According to the teachings herein, the liquid level adjustment device can discharge the priming solution from the venous air trap chamber. Accordingly, it is possible to reduce at least the overflow line within the dedicated components used for the automated priming, and the priming can be performed even in a state where the distal end of the arterial blood circuit and the distal end of the venous blood circuit are connected to each other.

BRIEF DESCRIPTION OF DRAWINGS

FIG. 1 is a schematic view illustrating a dialysis apparatus (blood purification apparatus) according to a first embodiment of the present invention.

FIG. 2 is a schematic view illustrating a state where priming (connection test step) is performed by the dialysis apparatus.

FIG. 3 is a schematic view illustrating a state where priming (first step) is performed by the dialysis apparatus.

FIG. 4 is a schematic view illustrating a state where priming (second step) is performed by the dialysis apparatus.

FIG. 5 is a schematic view illustrating a state where priming (third step) is performed by the dialysis apparatus.

FIG. 6 is a schematic view illustrating a state where priming (fourth step) is performed by the dialysis apparatus.

FIG. 7 is a schematic view illustrating a state where priming (gas purging step) is performed by the dialysis apparatus.

FIG. 8 is a schematic view illustrating a state where priming (preliminary step) suitable for the dialysis apparatus is performed.

FIG. 9 is a schematic view illustrating a state where priming (first step) is performed by a dialysis apparatus (blood purification apparatus) according to a second embodiment of the present invention.

FIG. 10 is a schematic view illustrating a state where priming (second step) is performed by the dialysis apparatus.

FIG. 11 is a schematic view illustrating a state where priming (third step) is performed by the dialysis apparatus.

FIG. 12 is a schematic view illustrating a state where priming (fourth step) is performed by the dialysis apparatus.

FIG. 13 is a schematic view illustrating a state where priming (second step) is performed by a dialysis apparatus (blood purification apparatus) according to a third embodiment of the present invention.

FIG. 14 is a schematic view illustrating a state where priming (third step) is performed by the dialysis apparatus.

FIG. 15 is a schematic view illustrating a state where priming (fourth step) is performed by the dialysis apparatus.

FIG. 16 is a schematic view illustrating a state where priming (second step) is performed by a dialysis apparatus (blood purification apparatus) according to a fourth embodiment of the present invention.

FIG. 17 is a schematic view illustrating a state where priming (third step) is performed by the dialysis apparatus.

FIG. 18 is a schematic view illustrating a state where priming (fourth step) is performed by the dialysis apparatus.

FIG. 19 is a schematic view illustrating a state where an additional step is performed by the dialysis apparatus.

FIG. 20 is a schematic view illustrating a state where priming (second and third steps) is performed by a dialysis apparatus (blood purification apparatus) according to a fifth embodiment of the present invention.

FIG. 21 is a schematic view illustrating a state where priming (fourth step) is performed by the dialysis apparatus.

FIG. 22 is a schematic view illustrating a state where priming (third step) is performed by a dialysis apparatus (blood purification apparatus) according to a sixth embodiment of the present invention.

FIG. 23 is a schematic view illustrating a state where priming (third step) is performed by a dialysis apparatus (blood purification apparatus) according to a seventh embodiment of the present invention.

FIG. 24 is a schematic view illustrating a state where priming (fourth step) is performed by the dialysis apparatus.

FIG. 25 is a schematic view illustrating a state where a cleaning step after treatment is performed by the dialysis apparatus.

FIG. 26 is a schematic view illustrating a state where priming (third step) is performed by a dialysis apparatus (blood purification apparatus) according to an eighth embodiment of the present invention.

FIG. 27 is a schematic view illustrating a state where priming (fourth step) is performed by the dialysis apparatus.

FIG. 28 is a schematic view illustrating a state where priming (third step) is performed by a dialysis apparatus (blood purification apparatus) according to a ninth embodiment of the present invention.

FIG. 29 is a schematic view illustrating a state where priming (fourth step) is performed by the dialysis apparatus.

DETAILED DESCRIPTION

Hereinafter, embodiments according to the present invention will be described in detail with reference to the drawings.

A blood purification apparatus according to a first embodiment includes a dialysis apparatus used for performing dialysis treatment. As illustrated in FIG. 1, the blood purification apparatus is mainly configured to have a blood circuit that includes an arterial blood circuit 1 and a venous blood circuit 2, a dialyzer 3 (blood purification device) that is interposed between the arterial blood circuit 1 and the venous blood circuit 2 and purifies blood flowing in the blood circuit, a peristaltic blood pump 4 that is arranged in the arterial blood circuit 1, an arterial air trap chamber 5 that is connected to the arterial blood circuit 1, a venous air trap chamber 6 that is connected to the venous blood circuit 2, a priming solution supplying line L3, a liquid level adjustment device A, and a control device C.

A connector a is connected to a distal end of the arterial blood circuit 1 to which an arterial puncture needle (not illustrated) can be connected via the connector a. The peristaltic blood pump 4 and the arterial air trap chamber 5 are arranged in an intermediate portion of the arterial blood circuit 1. In contrast, a connector b is connected to a distal end of the venous blood circuit 2 to which a venous puncture needle (not illustrated) can be connected via the connector b. The venous air trap chamber 6 is arranged in an intermediate portion of the venous blood circuit 2. The reference numerals S1 and S2 represent air bubble detectors used for detecting air bubbles flowing in a distal end portion of the arterial blood circuit 1 and a distal end portion of the venous blood circuit 2.

Then, if the blood pump 4 is rotated (normal rotation) in a state where the arterial puncture needle connected to the distal end of the arterial blood circuit 1 and the venous puncture needle connected to the distal end of the venous blood circuit 2 puncture a patient, blood of the patient reaches the dialyzer 3 after passing through the arterial blood circuit 1 while bubbles are removed in the arterial air trap chamber 5. After the blood is purified by the dialyzer 3, the blood is configured to return to an internal body of the patient after passing through the venous blood circuit 2 while bubbles are removed in the venous air trap chamber 6. In this manner, the dialyzer 3 can purify the blood of the patient by extracorporeally circulating the blood from the distal end of the arterial blood circuit 1 to the distal end of the venous blood circuit 2 in the blood circuit.

The liquid level adjustment device A is connected to each of the arterial air trap chamber 5 and the venous air trap chamber 6. The liquid level adjustment device A is incorporated in or externally attached to a dialysis device B, and is mainly configured to have an arterial air circulating line L8, a venous air circulating line L10, a release line L12 whose distal end is brought into an atmosphere released state, a communication line L9 which causes the arterial air circulating line L8 and the release line L12 to communicate with each other, a communication line L11 which causes the venous air circulating line L10 and the release line L12 to communicate with each other, and a liquid level adjustment pump 11.

The arterial air circulating line L8 is configured to have a flow route such as a flexible tube in which one end is connected to an upper portion (air layer side) of the arterial air trap chamber 5 and the other end is connected to an arterial pressure detection sensor 12. The arterial pressure detection sensor 12 can detect pressure of the upper portion (air layer side) of the arterial air trap chamber 5. In this manner, it is possible to detect the pressure of the blood flowing into the dialyzer 3 (pressure of an inlet in the dialyzer 3).

The venous air circulating line L10 is configured to have a flow route such as a flexible tube in which one end is connected to an upper portion (air layer side) of the venous air trap chamber 6 and the other end is connected to a venous pressure detection sensor 13. The venous pressure detection sensor 13 (a sensor which is a so-called "venous pressure sensor") can detect pressure of the upper portion (air layer side) of the venous air trap chamber 6. In this manner, it is possible to detect the pressure of the blood flowing in the venous blood circuit 2 (venous pressure).

The communication line L9 is configured to have a flow route such as a flexible tube in which one end is connected to an intermediate portion of the arterial air circulating line L8 and the other end is connected to a proximal end of the release line L12. In the intermediate portion thereof, an electromagnetic valve V9 which can open and close the flow route is arranged. In addition, the communication line L11 is configured to have a flow route such as a flexible tube in which one end is connected to an intermediate portion of the venous air circulating line L10 and the other end is connected to the proximal end of the release line L12. In the intermediate portion thereof, an electromagnetic valve V10 which can open and close the flow route is arranged.

The release line L12 is configured to have a flow route such as a flexible tube in which a proximal end is connected to each of the communication lines L9 and L11 and a distal end is brought into an atmosphere released state. In the intermediate portion thereof, the liquid level adjustment pump 11 configured to have a peristaltic pump is arranged. The liquid level adjustment pump 11 has a peristaltic unit which can perform normal rotation and reverse rotation. The peristaltic unit causes the flexible tube configuring the release line L12 to perform peristalsis in a longitudinal direction thereof. A configuration is made so that the peristaltic unit can optionally introduce or discharge the air to or from the upper portion of the arterial air trap chamber 5 or the upper portion of the venous air trap chamber 6. With regard to the liquid level adjustment pump 11, the drawing illustrates the normal rotation in case of clockwise rotation and the reverse rotation in case of counterclockwise rotation (similarly, with regard to the blood pump 4, the drawing illustrates the normal rotation in case of the clockwise rotation and the reverse rotation in case of the counterclockwise rotation).

If the liquid level adjustment pump 11 is normally rotated, the air is suctioned from the distal end of the release line L12. Accordingly, when the electromagnetic valve V9 is in an opened state, the air is introduced into the arterial air trap chamber 5, thereby lowering the liquid level. If the liquid level adjustment pump 11 is reversely rotated, the air is discharged from the distal end of the release line L12. Accordingly, when the electromagnetic valve V9 is in an opened state, the air is discharged from the arterial air trap chamber 5, thereby raising the liquid level.

Similarly, if the liquid level adjustment pump 11 is normally rotated, the air is suctioned from the distal end of the release line L12. Accordingly, when the electromagnetic valve V10 is in an opened state, the air is introduced into the venous air trap chamber 6, thereby lowering the liquid level. If the liquid level adjustment pump 11 is reversely rotated, the air is discharged from the distal end of the release line L12. Accordingly, when the electromagnetic valve V10 is in an opened state, the air is discharged from the venous air trap chamber 6, thereby raising the liquid level.

The dialyzer 3 is configured so that a housing unit thereof has a blood inlet 3a (blood inlet port), a blood outlet 3b (blood outlet port), a dialysate inlet 3c (inlet in dialysate flow route: dialysate inlet port), and a dialysate outlet 3d (outlet in dialysate flow route: dialysate outlet port). Among these, the arterial blood circuit 1 is connected to the blood inlet 3a, and the venous blood circuit 2 is connected to the blood outlet 3b, respectively. In addition, the dialysate inlet 3c and the dialysate outlet 3d are respectively connected to the dialysate introduction line L1 and the dialysate discharge line L2 which are disposed to extend from the dialysis device B.

The dialyzer 3 internally accommodates multiple hollow fiber membranes (not illustrated), and a hollow fiber thereof configures a blood purification membrane for purifying the blood. The dialyzer 3 internally has a blood flow route (flow route between the blood inlet 3a and the blood outlet 3b) in which the blood of a patient flows via the blood purification membrane and a dialysate flow route (flow route between the dialysate inlet 3c and the dialysate outlet 3d) in which the dialysate flows. Then, the hollow fiber membrane configuring the blood purification membrane has multiple minute apertures (pores) penetrating an outer peripheral surface and an inner peripheral surface thereof. A configuration is made so that impurities contained in the blood can permeate into the dialysate via the membrane.

The dialysis device B has the dialysate introduction line L1 and the dialysate discharge line L2, and has a duplex pump 7, bypass lines L4 to L7, and electromagnetic valves V3 to V8. Among these, the duplex pump 7 is arranged across the dialysate introduction line L1 and the dialysate discharge line L2. The duplex pump 7 serves to introduce the dialysate prepared to have a predetermined concentration to the dialyzer 3, and serves to discharge the dialysate used for dialysis from the dialyzer 3.

The electromagnetic valve V4 is connected to the intermediate portion of the dialysate introduction line L1 (between the connection portion with the priming solution supplying line L3 in the dialysate introduction line L1 and the dialyzer 3), and the electromagnetic valve V5 is connected to the intermediate portion of the dialysate discharge line L2 (between the connection portion with the bypass line L4 in the dialysate discharge line L2 and the dialyzer 3). In addition, filtration filters 8 and 9 are connected to a section between the duplex pump 7 and the electromagnetic valve V4 in the dialysate introduction line L1. The filtration filters 8 and 9 serve to filter and purify the dialysate flowing in the dialysate introduction line L1. The bypass lines L4 and L5 for introducing the dialysate to the dialysate discharge line L2 in a bypassing manner are respectively connected to an upstream side from the filtration filters 8 and 9. The electromagnetic valves V7 and V6 are respectively connected to the bypass lines L4 and L5.

Furthermore, the bypass lines L6 and L7 which bypass the duplex pump 7 are respectively connected to the dialysate discharge line L2. An ultrafiltration pump 10 for removing water from the patient's blood flowing in the blood flow route of the dialyzer 3 is arranged in the bypass line L6, and the electromagnetic valve V8 which can open and close the flow route is arranged in the bypass line L7. A pump (not illustrated) for adjusting liquid pressure on a liquid discharge side in the duplex pump 7 is arranged on the upstream side from the duplex pump 7 in the dialysate discharge line L2 (between the connection portion with the bypass line L5 and the duplex pump 7).

The priming solution supplying line L3 is configured to have a flow route such as a flexible tube which can supply the dialysate serving as the priming solution to the arterial blood circuit 1 and the venous blood circuit 2 during priming prior to treatment. The priming solution supplying line L3 is configured so that one end is connected to a predetermined portion in the dialysate introduction line L1 (between the filtration filter 9 and the electromagnetic valve V4) and the other end is connected to a predetermined portion of the arterial blood circuit 1 (between the electromagnetic valve V1 and the blood pump 4). An electromagnetic valve V11 which can open and close the flow route is arranged in the intermediate portion of the priming solution supplying line L3. A configuration is made so that the dialysate of the dialysate introduction line L1 can be supplied to the arterial blood circuit 1 and the venous blood circuit 2 when the electromagnetic valve V11 is in an opened state.

The electromagnetic valves V1 to V11 in the blood purification apparatus according to the present embodiment can open and close a flow route at each arranged position through opening and closing operations as described above, and are configured so that the opening and closing operations are controlled by the control device C such as a microcomputer. In particular, the control device C in the present embodiment is arranged inside the dialysis device B, and operates the liquid level adjustment device A during dialysis treatment (for example, during blood removal when extracorporeal circulating is started by collecting blood of a patient through an arterial puncture needle, or during blood returning when blood inside a blood circuit is returned to an internal body of a patient). The control device C is configured so that a liquid level formed inside the venous air trap chamber 6 (liquid level of blood) can be adjusted to have the height at any desired position.

That is, during the blood removal, the control device C controls the electromagnetic valves V9 and V10 to be in an opened state, and causes the liquid level adjustment pump 11 to be normally rotated so that the air can be introduced into the arterial air trap chamber 5 or into the venous air trap chamber 6, thereby lowering the liquid level. Alternatively, the control device C causes the liquid level adjustment pump 11 to be reversely rotated so that the air can be discharged from the arterial air trap chamber 5 or from the venous air trap chamber 6, thereby raising the liquid level. In this manner, the control device C can adjust the liquid level of liquid accumulation inside the arterial air trap chamber 5 or the venous air trap chamber 6 to have the height at any desired position.

Here, the control device C according to the present embodiment is configured to operate the liquid level adjustment device A at any desired timing during priming so that the arterial blood circuit 1, the venous blood circuit 2, and the dialyzer 3 interposed between the arterial blood circuit 1 and the venous blood circuit 2 can be filled with the priming solution (dialysate in the present embodiment) supplied from the priming solution supplying line L3. The priming means a step performed prior to treatment, and means cleaning work carried out by causing the priming solution such as the dialysate or the physiological saline solution to flow in the blood flow route or the dialysate flow route, and filling work carried out in advance by filling the blood flow route or the dialysate flow route with the priming solution.

Hereinafter, the priming according to the present embodiment will be described in detail.

First, the distal end of the arterial blood circuit 1 and the distal end of the venous blood circuit 2 are respectively released. As illustrated in FIG. 2, the control device C controls the electromagnetic valves V1, V3, V7, V9, and V10 to be in an opened state, and controls the electromagnetic valves V2, V4, V5, V6, V8, and V11 to be in a closed state. Thereafter, the control device C controls the liquid level adjustment pump 11 to be normally rotated (connection test step). At this time, the blood pump 4 and the duplex pump 7 are in a stopped state. At this time, it is preferable that the dialyzer 3 be attached so that the blood inlet 3a faces upward, similar to a case of treatment. If the dialyzer 3 is attached so that the blood inlet 3a faces upward, air bubble purging can be excellently performed during a gas purging step (to be described later).

According to the connection test step, predetermined pressure (positive pressure) can be applied to a portion illustrated by a thick line in FIG. 2. Accordingly, for example, it is possible to determine a connection state between the dialyzer 3 and the proximal end of the arterial blood circuit 1, and between the dialyzer 3 and the proximal end of the venous blood circuit 2. For example, when the predetermined pressure is applied, if a detection value of the arterial pressure detection sensor 12 or the venous pressure detection sensor 13 is not changed to reach a predetermined value (changed just a little bit), it is understood that the connection state of a certain portion illustrated by the thick line in the drawing is defective.

Then, after the test is carried out for the connection state of the priming solution supplying line L3 with the dialysate introduction line L1 and the connection state of a substitution line when the substitution line is present, as illustrated in FIG. 3, the control device C controls the electromagnetic valves V3, V7, V8, V9, and V11 to be in an opened state, and controls the electromagnetic valves V1, V2 V4, V5, V6, and V10 to be in a closed state. Thereafter, the control device C controls the liquid level adjustment pump 11 to be reversely rotated, the blood pump 4 to be normally rotated, and the duplex pump 7 to be rotated (first step). It is preferable to set the rotation speed of the liquid level adjustment pump 11 to be approximately the same as the rotation speed of the blood pump 4.

According to the first step, the dialysate of the dialysate introduction line L1 is supplied to the arterial blood circuit 1 via the priming solution supplying line L3, and the reverse rotation of the liquid level adjustment pump 11 causes the air inside the arterial air trap chamber 5 to be discharged outward. Accordingly, liquid accumulation is generated inside the arterial air trap chamber 5. Then, it is determined that the dialysate remaining inside the arterial air trap chamber 5 has reached a predetermined liquid level. Under the determined condition, the first step is completed.

It is possible to grasp a volume of the dialysate contained inside the arterial air trap chamber 5, based on the rotation speed and the rotation time period of the liquid level adjustment pump 11 and the blood pump 4. Accordingly, at the time when the volume reaches a predetermined amount, the first step may be completed. Alternatively, the first step may be completed by separately disposing a liquid level detection sensor in the arterial air trap chamber 5 at the time when the liquid level detection sensor detects a predetermined liquid level. In addition, a substitution line (flow route for pre-substitution) is connected to the arterial air trap chamber 5, and further the dialysate is introduced into the arterial air trap chamber 5 via the substitution line. In this manner, the priming may be performed on the substitution line concurrently with the blood circuit so that the liquid accumulation is generated in the arterial air trap chamber 5.

Thereafter, as illustrated in FIG. 4, the control device C controls the electromagnetic valves V2, V3, V7, V8, and V11 to be in an opened state, and controls the electromagnetic valves V1, V4, V5, V6, V9, and V10 to be in a closed state. Thereafter, the control device C controls the blood pump 4 to be normally rotated, the duplex pump 7 to maintain the rotation, and the liquid level adjustment pump 11 to stop the rotation (second step). According to the second step, the dialysate passing through the blood circuit of the dialyzer 3 also passes through the venous air trap chamber 6, and is discharged from the distal end of the venous blood circuit 2.

According to the second step, water-soluble impurities or air bubbles contained in the hollow fiber membrane (filtration membrane) of the dialyzer 3 together with the dialysate can be discharged from the distal end of the venous blood circuit 2, and the blood flow route of the dialyzer 3 can be filled with the dialysate. In the second step, if the electromagnetic valve V2 is controlled to be repeatedly in an opened state and off, the air bubbles inside the dialyzer 3 can be discharged efficiently. Accordingly, it is possible to perform further improved air purging.

Thereafter, as illustrated in FIG. 5, the control device C controls the electromagnetic valves V2, V3, V7, V8, V10, and V11 to be in an opened state, and controls the electromagnetic valves V1, V4, V5, V6, and V9 to be in a closed state. Thereafter, the control device C controls the liquid level adjustment pump 11 to be reversely rotated, the blood pump 4 to be normally rotated, and the duplex pump 7 to be rotated (third step). In the third step, similar to the first step, it is preferable to set the rotation speed of the liquid level adjustment pump 11 to be substantially the same as the rotation speed of the blood pump 4. However, the rotation speed of the liquid level adjustment pump 11 may be set to be slightly slower than the rotation speed of the blood pump 4. When the rotation speed of the liquid level adjustment pump 11 is set to be slightly slower than the rotation speed of the blood pump 4, the rotation of the blood pump 4 causes a surplus flow amount of the dialysate to be discharged from the connector b in the distal end of the venous blood circuit 2. In contrast, when the rotation speed of the liquid level adjustment pump 11 is set to be substantially the same as the rotation speed of the blood pump 4, the electromagnetic valve V2 may be in a closed state.

According to the third step, the dialysate of the dialysate introduction line L1 is supplied to the arterial blood circuit 1 and the venous blood circuit 2 via the priming solution supplying line L3, and the reverse rotation of the liquid level adjustment pump 11 causes the air inside the venous air trap chamber 6 to be discharged outward. Accordingly, liquid accumulation is generated inside the venous air trap chamber 6. Then, it is determined that the dialysate remaining inside the venous air trap chamber 6 has reached a predetermined liquid level. Under the determined condition, the third step is completed.

It is possible to grasp a volume of the dialysate contained inside the venous air trap chamber 6, based on the rotation speed and the rotation time period of the liquid level adjustment pump 11 and the blood pump 4. Accordingly, at the time when the volume reaches a predetermined amount, the third step may be completed. Alternatively, the third step may be completed by separately disposing a liquid level detection sensor in the venous air trap chamber 6 at the time when the liquid level detection sensor detects a predetermined liquid level. In addition, a substitution line (flow route for post-substitution) is connected to the venous air trap chamber 6, and further the dialysate is introduced into the venous air trap chamber 6 via the substitution line. In this manner, the priming may be performed on the substitution line concurrently with the blood circuit so that the liquid accumulation is generated in the venous air trap chamber 6. Furthermore, after the third step, the process may return to the second step so that cleaning is repeatedly performed using the priming solution (dialysate).

Thereafter, as illustrated in FIG. 6, the control device C controls the electromagnetic valves V1, V3, V8, and V11 to be in an opened state, and controls the electromagnetic valves V2, V4, V5, V6, V7, V9 and V10 to be in a closed state. Thereafter, the control device C controls the duplex pump 7 to maintain the rotation, and the liquid level adjustment pump 11 and the blood pump 4 to stop the rotation (fourth step). In the fourth step, the electromagnetic valve V2 may be in an opened state or in a closed state.

According to the fourth step, the dialysate of the dialysate introduction line L1 is supplied to the distal end portion (between the electromagnetic valve V1 and the connector a) of the arterial blood circuit 1 via the priming solution supplying line L3. Accordingly, the arterial blood circuit 1 and the venous blood circuit 2 (including the blood flow route in the dialyzer 3) can be entirely filled with the dialysate serving as the priming solution. The fourth step may be performed after the first step (that is, the first step, the fourth step, the second step, and the third step may be performed in this order).

As described above, the priming step is completed. Then, as illustrated in FIG. 7, the control device C controls the electromagnetic valves V3, V4, V5, V8, and V11 to be in an opened state, and controls the electromagnetic valves V1, V2, V6, V7, V9 and V10 to be in a closed state. Thereafter, the control device C controls the duplex pump 7 to maintain the rotation, the blood pump 4 to be normally rotated, and the liquid level adjustment pump 11 to stop the rotation (gas purging step).

According to the gas purging step, the dialysate flow route of the dialyzer 3 can be filled with the dialysate, and the rotation of the blood pump 4 causes the dialysate introduced into the arterial blood circuit 1 via the priming solution supplying line L3 to be filtered by the hollow fiber membrane (filtration membrane) of the dialyzer 3. Accordingly, pores (minute apertures) of the hollow fiber membrane can be cleaned at the same time. As described above, the priming and the gas purging are completed. Subsequently, the blood is extracorporeally circulated to start dialysis treatment (blood purification treatment).

In contrast, prior to the first step, as illustrated in FIG. 8, the control device C controls the electromagnetic valves V1, V3, V7, V8, and V10 to be in an opened state, and controls the electromagnetic valves V2, V4, V5, V6, V9 and V11 to be in a closed state. Thereafter, the control device C controls the blood pump 4 to be reversely rotated, the liquid level adjustment pump 11 to be normally rotated, and the duplex pump 7 to be rotated (preliminary step). Through the preliminary step, the filling solution inside the dialyzer 3 (in this case, wet type dialyzer filled with the filling solution) is suctioned into the arterial air trap chamber 5, thereby filling the flow route between the arterial air trap chamber 5 and the dialyzer 3 with the filling solution.

If the first step is about to start after the preliminary step is finished, since the flow route between the arterial air trap chamber 5 and the dialyzer 3 is filled with the filling solution, it is possible to prevent air bubbles from unintentionally flowing into the dialyzer 3. In the present embodiment, the duplex pump 7 is rotated. However, the preliminary step may be performed in a state where the duplex pump 7 is stopped. If the dialyzer attached to the blood circuit is a dry type (dialyzer which is not filled with the filling solution) instead of the wet type, a filling operation using the filling solution is not performed in the preliminary step. In addition to a case where the preliminary step is performed prior to the first step, the preliminary step may be performed after the first step (however, prior to the second step).

According to the above-described first embodiment, during the priming, the liquid level adjustment device A is operated at any desired timing so as to fill the arterial blood circuit 1 and the venous blood circuit 2 with the priming solution (dialysate) supplied from the priming solution supplying line L3. Accordingly, dedicated components used for automated priming can be reduced or dispensed with. Therefore, it is possible to reduce manufacturing costs of the blood circuit while achieving the automated priming.

Next, priming using a dialysis apparatus (blood purification apparatus) according to a second embodiment of the present invention will be described.

As illustrated in FIGS. 9 to 12, the liquid level adjustment device A employed in the present embodiment is mainly configured to have the arterial air circulating line L8, the venous air circulating line L10, the arterial pressure detection sensor 12 connected to the other end of the arterial air circulating line L8, the venous pressure detection sensor 13 connected to the other end of the venous air circulating line L10, the communication line L9 in which one end is connected to an intermediate portion of the arterial air circulating line L8 and the other end is brought into an atmosphere released state, the communication line L11 in which one end is connected to an intermediate portion of the venous air circulating line L10 and the other end is brought into an atmosphere released state, the electromagnetic valve V9 which can open and close the flow route of the communication line L9, and the electromagnetic valve V10 which can open and close the communication line L11.

That is, the liquid level adjustment device A employed in the present embodiment does not include the pump serving as an actuator, unlike the liquid level adjustment pump 11 according to the first embodiment. If the liquid level adjustment device A is operated during dialysis treatment, the electromagnetic valve V9 and the electromagnetic valve V10 are just in an opened state and off. In this manner, a configuration is made so that a liquid level formed inside the arterial air trap chamber 5 or the venous air trap chamber 6 can be adjusted to have the height at any desired position.

In the present embodiment, when the priming is performed, the distal end of the arterial blood circuit 1 and the distal end of the venous blood circuit 2 are respectively brought into a released state as illustrated in FIG. 9, and the connection test step in the first embodiment is performed. Thereafter, as illustrated in the drawing, the control device C controls the electromagnetic valves V3, V7, V8, V9, and V11 to be in an opened state, and controls the electromagnetic valves V1, V2, V4, V5, V6, and V10 to be in a closed state. Thereafter, the control device C controls the blood pump 4 to be normally rotated and the duplex pump 7 to be rotated (first step). The electromagnetic valve V2 may be in an opened state or in a closed state. However, if the electromagnetic valve V2 is in a closed state as in the present embodiment, it is possible to reliably form liquid accumulation inside the venous air trap chamber 6. Thereafter, as illustrated in FIG. 10, the control device C controls the electromagnetic valves V2, V3, V7, V8, and V11 to be in an opened state, and controls the electromagnetic valves V1, V4, V5, V6, V9, and V10 to be in a closed state. Thereafter, the control device C controls the blood pump 4 to be normally rotated and the duplex pump 7 to maintain the rotation (second step).

Then, as illustrated in FIG. 11, the control device C controls the electromagnetic valves V2, V3, V7, V8, V10, and V11 to be in an opened state, and controls the electromagnetic valves V1, V4, V5, V6, and V9 to be in a closed state. The control device C controls the blood pump 4 to be normally rotated and the duplex pump 7 to maintain the rotation (third step). The electromagnetic valve V2 may be in an opened state or in a closed state. However, if the electromagnetic valve V2 is in a dosed state, it is possible to reliably form liquid accumulation inside the venous air trap chamber 6. Thereafter, as illustrated in FIG. 12, the control device C controls the electromagnetic valves V1, V3, V5, and V11 to be in an opened state, and controls the electromagnetic valves V2, V4, V5, V6, V7, V9, and V10 to be in a dosed state. Thereafter, the control device C controls the duplex pump 7 to maintain the rotation and the blood pump 4 to stop the rotation (fourth step).

According to the above-described second embodiment, even if the liquid level adjustment device A does not include the actuator such as the liquid level adjustment pump, the liquid level adjustment device A is operated at any desired timing during the priming. In this manner, the arterial blood circuit 1 and the venous blood circuit 2 are filled with the priming solution (dialysate) supplied from the priming solution supplying line L3. Accordingly, dedicated components used for automated priming can be reduced or dispensed with. Therefore, it is possible to reduce manufacturing costs of the blood circuit while achieving the automated priming.

Next, priming using a dialysis apparatus (blood purification apparatus) according to a third embodiment of the present invention will be described.

As illustrated in FIGS. 13 to 15, the liquid level adjustment device A employed in the present embodiment is mainly configured to have the venous air circulating line L10, the venous pressure detection sensor 13 connected to the other end of the venous air circulating line L10, a release line L12 in which a distal end is brought into an atmosphere released state and the liquid level adjustment pump 11 is arranged, the communication line L11 in which one end is connected to the intermediate portion of the venous air circulating line L10 and the other end is connected to a proximal end of the release line L12, and the electromagnetic valve V10 which can open and close the communication line L11.

That is, the liquid level adjustment device A employed in the present embodiment does not include the arterial air circulating line L8 and the arterial pressure detection sensor 12 which are connected to the upper portion of the arterial air trap chamber 5, unlike the liquid level adjustment pump 11 according to the first embodiment. If the liquid level adjustment device A is operated during dialysis treatment, the liquid level adjustment pump 11 is normally rotated or reversely rotated, and the electromagnetic valve V10 is in an opened state and off. In this manner, a configuration is made so that a liquid level formed inside the venous air trap chamber 6 can be adjusted to have the height at any desired position.

In the present embodiment, when the priming is performed, the distal end of the arterial blood circuit 1 and the distal end of the venous blood circuit 2 are respectively brought into a released state as illustrated in FIG. 13, and the arterial air trap chamber 5 is brought into a vertically inverted state. After the connection test step in the first embodiment is performed, as illustrated in the drawing, the control device C controls the electromagnetic valves V2, V3, V7, V8, and V11 to be in an opened state, and controls the electromagnetic valves V1, V4, V5, V6, and V10 to be in a closed state. Thereafter, the control device C controls the blood pump 4 to be normally rotated, the duplex pump 7 to be rotated, and the liquid level adjustment pump 11 to stop the rotation (second step).

Then, as illustrated in FIG. 14, the control device C controls the electromagnetic valves V2, V3, V7, V8, V10, and V11 to be in an opened state, and controls the electromagnetic valves V1, V4, V5, and V6 to be in a closed state. The control device C controls the liquid level adjustment pump 11 to be reversely rotated, the blood pump 4 to be normally rotated, and the duplex pump 7 to maintain the rotation (third step). The electromagnetic valve V2 may be in an opened state or in a closed state. However, if the electromagnetic valve V2 is in a closed state, it is possible to reliably form liquid accumulation inside the venous air trap chamber 6. Thereafter, as illustrated in FIG. 15, the control device C controls the electromagnetic valves V1, V3, V8, and V11 to be in an opened state, and controls the electromagnetic valves V2, V4, V5, V6, V7, and V10 to be in a closed state. Thereafter, the control device C controls the duplex pump 7 to maintain the rotation, and the liquid level adjustment pump 11 and the blood pump 4 to stop the rotation (fourth step). The dialysis treatment is performed by vertically inverting the arterial air trap chamber 5 so as to return to its original state.

According to the above-described third embodiment, even if the liquid level adjustment device A does not include the arterial air circulating line L8 and the arterial pressure detection sensor 12 which are connected to the arterial air trap chamber 5, the liquid level adjustment device A is operated at any desired timing during the priming. In this manner, the arterial blood circuit 1 and the venous blood circuit 2 are filled with the priming solution (dialysate) supplied from the priming solution supplying line L3. Accordingly, dedicated components used for automated priming can be reduced or dispensed with. Therefore, it is possible to reduce manufacturing costs of the blood circuit while achieving the automated priming.

Next, priming using a dialysis apparatus (blood purification apparatus) according to a fourth embodiment of the present invention will be described.

As illustrated in FIGS. 16 to 18, the liquid level adjustment device A employed in the present embodiment is mainly configured to have the venous air circulating line L10, the venous pressure detection sensor 13 connected to the other end of the venous air circulating line L10, the release line L12 in which a distal end is brought into an atmosphere released state and the liquid level adjustment pump 11 is arranged, the communication line L11 in which one end is connected to the intermediate portion of the venous air circulating line L10 and the other end is connected to the proximal end of the release line L12, and the electromagnetic valve V10 which can open and close the communication line L11.

That is, similar to the third embodiment, the liquid level adjustment device A employed in the present embodiment does not include the arterial air circulating line L8 and the arterial pressure detection sensor 12 which are connected to the upper portion of the arterial air trap chamber 5, unlike the liquid level adjustment pump 11 according to the first embodiment. If the liquid level adjustment device A is operated during dialysis treatment, the liquid level adjustment pump 11 is normally rotated or reversely rotated, and the electromagnetic valve V10 is in an opened state and off. In this manner, a configuration is made so that a liquid level formed inside the venous air trap chamber 6 can be adjusted to have the height at any desired position.

In the present embodiment, when the priming is performed, the distal end of the arterial blood circuit 1 and the distal end of the venous blood circuit 2 are respectively brought into a released state as illustrated in FIG. 16, and the connection test step in the first embodiment is performed. Thereafter, as illustrated in the drawing, the control device C controls the electromagnetic valves V2, V3, V7, V8, and V11 to be in an opened state, and controls the electromagnetic valves V1, V4, V5, V6, and V10 to be in a closed state. Thereafter, the control device C controls the blood pump 4 to be normally rotated, the duplex pump 7 to be rotated, and the liquid level adjustment pump 11 to stop the rotation (second step).

At this time, if the rotation speed of the blood pump 4 is set to be relatively faster (for example, rotation speed of 200 mL/min), flow resistance of the dialysate flowing in the flow route between the arterial air trap chamber 5 and the dialyzer 3 increases. Accordingly, it is possible to generate liquid accumulation inside the arterial air trap chamber 5. In this manner, even if the arterial air circulating line L8 of the liquid level adjustment device A is not connected to the arterial air trap chamber 5, it is possible to generate the liquid accumulation having a predetermined liquid level inside the arterial air trap chamber 5.

Then, as illustrated in FIG. 17, the control device C controls the electromagnetic valves V2, V3, V7, V8, V10, and V11 to be in an opened state, and controls the electromagnetic valves V1, V4, V5, and V6 to be in a closed state. The control device C controls the liquid level adjustment pump 11 to be reversely rotated, the blood pump 4 to be normally rotated, and the duplex pump 7 to maintain the rotation (third step). The electromagnetic valve V2 may be in an opened state or in a closed state. However, if the electromagnetic valve V2 is in a closed state, it is possible to reliably form liquid accumulation inside the venous air trap chamber 6. Thereafter, as illustrated in FIG. 18, the control device C controls the electromagnetic valves V1, V3, V8, and V11 to be in an opened state, and controls the electromagnetic valves V2, V4, V5, V6, V7, and V10 to be in a closed state. Thereafter, the control device C controls the duplex pump 7 to maintain the rotation, and the liquid level adjustment pump 11 and the blood pump 4 to stop the rotation (fourth step).

According to the above-described fourth embodiment, even if the liquid level adjustment device A does not include the arterial air circulating line L8 and the arterial pressure detection sensor 12 which are connected to the arterial air trap chamber 5, the liquid level adjustment device A is operated at any desired timing during the priming. In this manner, the arterial blood circuit 1 and the venous blood circuit 2 are filled with the priming solution (dialysate) supplied from the priming solution supplying line L3. Accordingly, dedicated components used for automated priming can be reduced or dispensed with. Therefore, it is possible to reduce manufacturing costs of the blood circuit while achieving the automated priming.

In the above-described fourth embodiment, after the above-described fourth step, it is preferable to add a step in which as illustrated in FIG. 19, after the control device C controls the electromagnetic valves V1, V3, V4, V7, and V8 to be in an opened state, and controls the electromagnetic valves V2, V5, V6, V10, and V11 to be in a closed state, the control device C controls the duplex pump 7 to be rotated, the liquid level adjustment pump 11 to maintain the stopped state, and the blood pump 4 to be reversely rotated. If the step is added, the dialysate of the dialysate introduction line L1 can be introduced (filtered from the dialysate flow route to the blood flow route) via the dialyzer 3 so as to flow into the arterial air trap chamber 5. In this manner, liquid accumulation can be sufficiently secured in the arterial air trap chamber 5. Accordingly, it is possible to adjust the liquid level to be a desired liquid level, and it is possible to remove air bubbles in the dialyzer 3 (particularly, in the vicinity of the blood inlet 3a).

According to the above-described first to fourth embodiments, during the priming, the distal end of the arterial blood circuit 1 and the distal end of the venous blood circuit 2 are respectively brought into a released state, and the priming solution (dialysate) supplied from the priming solution supplying line L3 is discharged from the distal end of the arterial blood circuit 1 and the distal end of the venous blood circuit 2. Accordingly, within the dedicated components used for the automated priming, it is possible to dispense with at least an overflow line and a connection instrument for connecting the distal end of the arterial blood circuit 1 and the distal end of the venous blood circuit 2 to each other.

Next, priming using a dialysis apparatus (blood purification apparatus) according to a fifth embodiment of the present invention will be described.

As illustrated in FIGS. 20 and 21, the dialysis apparatus according to the present embodiment is the same as that in the first embodiment, with regard to the liquid level adjustment device A and other configurations. However, in the present embodiment, as illustrated in the drawing, during the priming, the distal end of the arterial blood circuit 1 and the distal end of the venous blood circuit 2 are brought into a mutually connected state.

Then, after the connection test step in the first embodiment is performed, the control device C controls the same step as the first step in the first embodiment to be performed. Thereafter, as illustrated in FIG. 20, the control device C controls the electromagnetic valves V2, V3, V7, V8, V10, and V11 to be in an opened state, and controls the electromagnetic valves V1, V4, V5, V6, and V9 to be in a dosed state. The control device C controls the blood pump 4 to be normally rotated, the liquid level adjustment pump 11 to be reversely rotated, and the duplex pump 7 to be rotated (second and third steps).

At this time, the liquid level adjustment device A is configured so that the air or the priming solution (dialysate) is discharged from the venous air trap chamber 6 via the venous air circulating line L10, the communication line L11, and the release line L12. In this manner, the priming solution (dialysate) supplied from the priming solution supplying line L3 becomes the liquid accumulation in the arterial air trap chamber 5 and the venous air trap chamber 6, and the air or the priming solution (dialysate) is discharged outward via the liquid level adjustment device A.

Thereafter, as illustrated in FIG. 21, the control device C controls the electromagnetic valves V1, V2, V3, V7, V8, V10, and V11 to be in an opened state, and controls the electromagnetic valves V4, V5, V6, and V9 to be in a closed state. Thereafter, the control device C controls the liquid level adjustment pump 11 to be reversely rotated, the duplex pump 7 to maintain the rotation, and the blood pump 4 to stop the rotation (fourth step). Even in the fourth step, the priming solution (dialysate) supplied from the priming solution supplying line L3 becomes the liquid accumulation in the venous air trap chamber 6, and the air or the priming solution (dialysate) is discharged outward via the liquid level adjustment device A.

According to the above-described fifth embodiment, even when the distal end of the arterial blood circuit 1 and the distal end of the venous blood circuit 2 are brought into a mutually connected state, the liquid level adjustment device A is operated at any desired timing during the priming. In this manner, the arterial blood circuit 1 and the venous blood circuit 2 are filled with the priming solution (dialysate) supplied from the priming solution supplying line L3. Accordingly, dedicated components used for automated priming can be reduced or dispensed with. Therefore, it is possible to reduce manufacturing costs of the blood circuit while achieving the automated priming.

In particular, according to the fifth embodiment, the liquid level adjustment device A can discharge the priming solution from the venous air trap chamber 6. Accordingly, since the same function as an overflow line in the related art can be provided, it is possible to reduce at least an overflow line within the dedicated components used for the automated priming. Even in a state where the distal end of the arterial blood circuit 1 and the distal end of the venous blood circuit 2 are connected to each other, the priming can be performed.

According to the above-described first and third to fifth embodiments, the liquid level adjustment device A includes the liquid level adjustment pump 11 which can be normally rotated and can be reversely rotated. During the priming, the liquid level adjustment pump 11 is operated at any desired timing so as to introduce or discharge the air to or from the upper portion of the venous air trap chamber 6 (in the first and fifth embodiments, the arterial air trap chamber 5 is also included). Accordingly, an optimal amount of the air can be introduced to or discharged from the venous air trap chamber 6 during treatment and during the priming.

In addition, according to the above-described first, second, and fifth embodiments, the arterial air trap chamber 5 is connected to the arterial blood circuit 1, and the liquid level adjustment device A is connected to each of the arterial air trap chamber 5 and the venous air trap chamber 6 so that each liquid level formed inside the arterial air trap chamber 5 and the venous air trap chamber 6 is adjusted to have the height at any desired position. Accordingly, each liquid level in the arterial air trap chamber 5 and the venous air trap chamber 6 can be adjusted to have the optimal height during the treatment and during the priming.

Furthermore, according to the above-described first to fifth embodiments, the priming solution supplying line L3 is configured so that one end is connected to the dialysate introduction line L1 and the other end is connected to a predetermined portion of the blood circuit (specifically, a portion between the blood pump 4 and the electromagnetic valve V1 in the arterial blood circuit 1), and supplies the dialysate of the dialysate introduction line L1 to the arterial blood circuit 1 and the venous blood circuit 2. Accordingly, as compared to a case where a physiological saline solution is supplied as the priming solution, automated priming can be more smoothly achieved.

In particular, according to the above-described first to fifth embodiments, it is possible to dispense with a clamp device which is to be mounted on an overflow line dedicated for priming as in the related art. Accordingly, a health care worker can save time to mount the clamp device on the overflow line, and can avoid a failure in automated priming which is caused by the health care worker having forgotten to mount the clamp device on the overflow line.

Next, priming using a dialysis apparatus (blood purification apparatus) according to a sixth embodiment of the present invention will be described.

As illustrated in FIG. 22, the dialysis apparatus according to the present embodiment is substantially the same as that in the first embodiment, with regard to the liquid level adjustment device A and other configurations. However, in the present embodiment, when the priming is performed, as illustrated in the drawing, a distal end (connector a) of the arterial blood circuit 1 is brought into a state of being connected to a predetermined portion of the dialysate introduction line L1 (in the present embodiment, a to-be-connected portion X between the filtration filter 9 and the electromagnetic valve 4). The dialysis apparatus does not include the priming solution supplying line L3 and the electromagnetic valve V11.

Then, after the connection test step in the first embodiment is performed, the control device C controls the same step as the first step and the second step in the first embodiment to be performed. Thereafter, as illustrated in FIG. 22, the control device C controls the electromagnetic valves V1, V2, V3, V7, V8, and V10 to be in an opened state, and controls the electromagnetic valves V4, V5, V6, and V9 to be in a closed state. The control device C controls the blood pump 4 to be normally rotated, the liquid level adjustment pump 11 to be reversely rotated, and the duplex pump 7 to be rotated (third step).

At this time, the liquid level adjustment device A is configured so that the air or the priming solution (dialysate) is discharged from the venous air trap chamber 6 via the venous air circulating line L10, the communication line L11, and the release line L12. In this manner, the priming solution (dialysate) supplied from the arterial blood circuit 1 becomes the liquid accumulation in the arterial air trap chamber 5 and the venous air trap chamber 6, and the air or the priming solution (dialysate) is discharged outward via the liquid level adjustment device A.

According to the above-described sixth embodiment, the fourth step in the priming according to the first to fifth embodiments can be omitted, and it is possible to dispense with the priming solution supplying line L3 and the electromagnetic valve V11 which are needed during the priming according to the first to fifth embodiments. Therefore, it is possible to shorten the time required for the priming by omitting the fourth step, thereby enabling the apparatus configuration to be simplified. In the present embodiment, the dialysate introduction line L1 serves as the priming solution supplying line L3.

Next, priming using a dialysis apparatus (blood purification apparatus) according to a seventh embodiment of the present invention will be described.

As illustrated in FIGS. 23 and 24, the dialysis apparatus according to the present embodiment is substantially the same as that in the first embodiment, with regard to the liquid level adjustment device A and other configurations. However, in the present embodiment, when the priming is performed, as illustrated in the drawing, a distal end (connector a) of the arterial blood circuit 1 and a distal end (connector b) of the venous blood circuit 2 are brought into a state of being connected to a predetermined portion of the dialysate discharge line L2 (in the present embodiment, to-be-connected portions α1 and β1).

The to-be-connected portions α1 and β1 in the present embodiment are located on a downstream side from the duplex pump 7 (pump which discharges the dialysate from the dialyzer to the dialysate discharge line L2) in the dialysate discharge line L2. During the priming, the distal end (connector a) of the arterial blood circuit 1 and the distal end (connector b) of the venous blood circuit 2 are respectively connected to the to-be-connected portions α1 and β1. In this manner, a configuration is made so that the distal end (connector a) of the arterial blood circuit 1 and the distal end (connector b) of the venous blood circuit 2 are connected to the downstream side from the duplex pump 7 in the dialysate discharge line L2.

Furthermore, in the present embodiment, there is provided a connection line L13 which connects the upstream side from the duplex pump 7 in the dialysate introduction line L1 and the downstream side from the duplex pump 7 in the dialysate discharge line L2 to each other. An electromagnetic valve V12 is arranged in the connection line L13. Electromagnetic valves 13 and 14 are respectively arranged on the upstream side from a connection portion with the connection line L13 in the dialysate introduction line L1 and the downstream side from a connection portion with the connection line L13 in the dialysate discharge line L2.

Then, during the priming, the connector a of the distal end of the arterial blood circuit 1 is connected to the to-be-connected portion α1 in the dialysate discharge line L2, and the connector b of the distal end of the venous blood circuit 2 is connected to the to-be-connected portion β1 in the dialysate discharge line L2. After the connection test step in the first embodiment is performed, the control device C controls the same step as the first step in the first embodiment to be performed. Thereafter, as illustrated in FIG. 23, the control device C controls the electromagnetic valves V2, V3, V7, V8, V11, V13, and V14 to be in an opened state, and controls the electromagnetic valves V1, V4, V5, V6, V9, V10, and V12 to be in a closed state. Thereafter, the control device C controls the blood pump 4 to be normally rotated and the duplex pump 7 to be rotated (the liquid level adjustment pump 11 is stopped). In this manner, the second step can be performed. In a state illustrated in FIG. 23, the control device C controls the electromagnetic valve V10 to be in an opened state and the liquid level adjustment pump 11 to be reversely rotated. In this manner, the third step can be performed. In the second and third steps, the priming solution (dialysate) supplied from the priming solution supplying line L3 flows in the arterial blood circuit 1, the dialysate flow route of the dialyzer 3, and the venous blood circuit 2, and then, is discharged from the distal end (connector b) of the venous blood circuit 2 via the dialysate discharge line L2.

Thereafter, as illustrated in FIG. 24, the control device C controls the electromagnetic valves V1, V3, V7, V8, V11, V13, and V14 to be in an opened state, and controls the electromagnetic valves V2, V4, V5, V6, V9, V10, and V12 to be in a closed state. Thereafter, the control device C controls the blood pump 4 and the liquid level adjustment pump 11 to stop the rotation, and the duplex pump 7 to be rotated. In this manner, the fourth step can be performed. In the fourth step, the priming solution (dialysate) supplied from the priming solution supplying line L3 flows in the upstream side (connector a side) from the connection portion with the priming solution supplying line L3 in the arterial blood circuit 1, and then, is discharged from the distal end (connector a) of the arterial blood circuit 1 via the dialysate discharge line L2.

According to the above-described seventh embodiment, during the priming, the distal end of the arterial blood circuit 1 and the distal end of the venous blood circuit 2 are respectively connected to the dialysate discharge line L2. The priming solution (dialysate) supplied from the priming solution supplying line L3 is discharged from the distal end of the arterial blood circuit 1 and the distal end of the venous blood circuit 2 via the dialysate discharge line L2. Accordingly, the priming solution used during the priming can be discharged using the dialysate discharge line L2. Therefore, the priming solution can be easily collected.

In addition, according to the above-described seventh embodiment, the dialysate discharge line L2 includes the duplex pump 7 which discharges the dialysate from the dialyzer 3 to the dialysate discharge line L2. During the priming, the distal end of the arterial blood circuit 1 and the distal end of the venous blood circuit 2 are connected to the downstream side from the duplex pump 7 in the dialysate discharge line L2. Accordingly, it is possible to reliably avoid a case where the priming solution discharged from the distal end of the arterial blood circuit 1 and the distal end of the venous blood circuit 2 unintentionally reaches the dialyzer 3.

In contrast, in the above-described seventh embodiment, there is provided the connection line L13 which connects the upstream side from the duplex pump 7 in the dialysate introduction line L1 and the downstream side from the duplex pump 7 in the dialysate discharge line L2, the electromagnetic valve V12 is arranged in the connection line L13, and the electromagnetic valves V13 and V14 are respectively arranged in the dialysate introduction line L1 and the dialysate discharge line L2. Accordingly, as illustrated in FIG. 25, during a cleaning step after hemodialysis treatment is completed, cleaning solution can be circulated in the dialysate introduction line L1, the dialysate discharge line L2, and the connection line L13.

That is, during the cleaning step after the treatment, the control device C controls a short circuit to be caused by connecting the distal end of the dialysate introduction line L1 and the distal end of the dialysate discharge line L2 to a coupler D. The control device C controls the electromagnetic valves V3, V7, V8, and V12 to be in an opened state, and controls the electromagnetic valves V4, V5, V6, V13, and V14 to be in a closed state. The duplex pump 7 is rotated so that the cleaning solution is circulated in the circulating flow route including the to-be-connected portions α1 and β1, thereby enabling the cleaning to be performed. If disinfecting solution is circulated in place of the cleaning solution, the circulating flow route including the to-be-connected portions α1 and β1 can be disinfected.

Next, priming using a dialysis apparatus (blood purification apparatus) according to an eighth embodiment of the present invention will be described.

As illustrated in FIGS. 26 and 27, the dialysis apparatus according to the present embodiment is substantially the same as that in the seventh embodiment, with regard to the liquid level adjustment device A and other configurations. However, in the present embodiment, when the priming is performed, as illustrated in the drawing, the distal end (connector a) of the arterial blood circuit 1 and the distal end (connector b) of the venous blood circuit 2 are brought into a state of being connected to a predetermined portion of the connection line L13 branched from the dialysate discharge line L2 (in the present embodiment, to-be-connected portions α2 and β2 of the connection line L13).

The to-be-connected portions α2 and β2 in the present embodiment are respectively located in the connection line L13 which connects the upstream side from the duplex pump 7 in the dialysate introduction line L1 and the downstream side from the duplex pump 7 in the dialysate discharge line L2. During the priming, the distal end (connector a) of the arterial blood circuit 1 and the distal end (connector b) of the venous blood circuit 2 are respectively connected to the to-be-connected portions α2 and β2. In this manner, a configuration is made so that the distal end (connector a) of the arterial blood circuit 1 and the distal end (connector b) of the venous blood circuit 2 are connected to the connection line L13.

Furthermore, electromagnetic valves V15 and V16 are arranged in the connection line L13 according to the present embodiment, and the to-be-connected portions α2 and β2 are formed between the electromagnetic valves V15 and V16. Similar to the seventh embodiment, the electromagnetic valves V13 and V14 are respectively arranged on the upstream side from the connection portion with the connection line L13 in the dialysate introduction line L1 and the downstream side from the connection portion with the connection line L13 in the dialysate discharge line L2.

Then, during the priming, the connector a of the distal end of the arterial blood circuit 1 is connected to the to-be-connected portion α2 in the connection line L13, and the connector b of the distal end of the venous blood circuit 2 is connected to the to-be-connected portion β2 in the connection line L13. After the connection test step in the first embodiment is performed, the control device C controls the same step as the first step in the first embodiment to be performed. Thereafter, as illustrated in FIG. 26, the control device C controls the electromagnetic valves V2, V3, V7, V8, V11, V13, V14, and V16 to be in an opened state, and controls the electromagnetic valves V1, V4, V5, V6, V9, V10, and V15 to be in a dosed state. Thereafter, the control device C controls the blood pump 4 to be normally rotated and the duplex pump 7 to be rotated (the liquid level adjustment pump 11 is stopped). In this manner, the second step can be performed. In a state illustrated in FIG. 26, the control device C controls the electromagnetic valve V10 to be in an opened state and the liquid level adjustment pump 11 to be reversely rotated. In this manner, the third step can be performed. In the second and third steps, the priming solution (dialysate) supplied from the priming solution supplying line L3 flows in the arterial blood circuit 1, the dialysate flow route of the dialyzer 3, and the venous blood circuit 2, then flows in the connection line L13 from the distal end (connector b) of the venous blood circuit 2, and is discharged via the dialysate discharge line L2.

Thereafter, as illustrated in FIG. 27, the control device C controls the electromagnetic valves V1, V3, V7, V8, V11, V13, V14 and V16 to be in an opened state, and controls the electromagnetic valves V2, V4, V5, V6, V9, V10, and V15 to be in a closed state. Thereafter, the control device C controls the blood pump 4 and the liquid level adjustment pump 11 to stop the rotation, and the duplex pump 7 to be rotated. In this manner, the fourth step can be performed. In the fourth step, the priming solution (dialysate) supplied from the priming solution supplying line L3 flows in the upstream side (connector a side) from the connection portion with the priming solution supplying line L3 in the arterial blood circuit 1, then flows in the connection line L13 from the distal end (connector a) of the arterial blood circuit 1, and is discharged via the dialysate discharge line L2.

According to the above-described eighth embodiment, during the priming, the distal end of the arterial blood circuit 1 and the distal end of the venous blood circuit 2 are respectively connected to the connection line L13. The priming solution (dialysate) supplied from the priming solution supplying line L3 is discharged from the distal end of the arterial blood circuit 1 and the distal end of the venous blood circuit 2 via the dialysate discharge line L2 (strictly speaking, discharged from the distal end of the arterial blood circuit 1 and the distal end of the venous blood circuit 2 via the connection line L13 and the dialysate discharge line L2). Accordingly, the priming solution used during the priming can be discharged using the dialysate discharge line L2. Therefore, the priming solution can be easily collected.

In addition, according to the above-described eighth embodiment, the dialysate discharge line L2 includes the duplex pump 7 which discharges the dialysate from the dialyzer 3 to the dialysate discharge line L2. During the priming, the distal end of the arterial blood circuit 1 and the distal end of the venous blood circuit 2 are connected to the connection line L13 located on the downstream side from the duplex pump 7 in the dialysate discharge line L2 (to be located on the downstream side from the duplex pump 7 since the electromagnetic valve V15 is in a closed state). Accordingly, it is possible to reliably avoid a case where the priming solution discharged from the distal end of the arterial blood circuit 1 and the distal end of the venous blood circuit 2 unintentionally reaches the dialyzer 3.

Next, priming using a dialysis apparatus (blood purification apparatus) according to a ninth embodiment of the present invention will be described.

As illustrated in FIGS. 28 and 29, the dialysis apparatus according to the present embodiment is substantially the same as that in the eighth embodiment, with regard to the liquid level adjustment device A and other configurations. However, in the present embodiment, when the priming is performed, as illustrated in the drawing, the distal end (connector a) of the arterial blood circuit 1 and the distal end (connector b) of the venous blood circuit 2 are brought into a state of being connected to a predetermined portion of the connection line L13 via a connection device La (in the present embodiment, to-be-connected portion γ of the connection line L13).

The to-be-connected portion γ in the present embodiment is located in the connection line L13 which connects the upstream side from the duplex pump 7 in the dialysate introduction line L1 and the downstream side from the duplex pump 7 in the dialysate discharge line L2. During the priming, the distal end (connector a) of the arterial blood circuit 1 and the distal end (connector b) of the venous blood circuit 2 are connected to the to-be-connected portion γ via the connection device La. In this manner, a configuration is made so that the distal end (connector a) of the arterial blood circuit 1 and the distal end (connector b) of the venous blood circuit 2 are connected to the connection line L13.

Furthermore, the electromagnetic valves V15 and V16 are arranged in the connection line L13 according to the present embodiment, and the to-be-connected portion γ is formed between the electromagnetic valves V15 and V16. Similar to the seventh and eighth embodiments, the electromagnetic valves V13 and V14 are respectively arranged on the upstream side from the connection portion with the connection line L13 in the dialysate introduction line L1 and the downstream side from the connection portion with the connection line L13 in the dialysate discharge line L2.

Here, the connection device La according to the present embodiment is configured to have a Y-shaped tube (separate tube) including a first connection portion α3 and a second connection portion β3 which can be respectively connected to the connector a of the distal end of the arterial blood circuit 1 and the connector b of the distal end of the venous blood circuit 2, and a third connection portion Laa which can be connected to the to-be-connected portion γ of the connection line L13. In the present embodiment, the connection device La is configured to have the Y-shaped tube (tube in which a pair of the first connection portion α3 and the second connection portion β3 are formed on one end side and the third connection portion Laa alone is formed on the other end side). However, the connection device La may be configured to have two tubes including a tube in which one end can be connected to the connector a of the distal end of the arterial blood circuit 1 and the other end can be connected to the connection line L13, and a tube in which one end can be connected to the connector b of the distal end of the venous blood circuit 2 and the other end can be connected to the connection line L13 (in this case, two of the to-be-connected portions are required in the connection line L13). In addition, the connection device La according to the present embodiment can connect the third connection portion Laa to the connection line L13 during the priming. However, the third connection portion Laa may be connected to the dialysate discharge line L2 by forming the to-be-connected portion in the dialysate discharge line L2.

Then, during the priming, the connector a of the distal end of the arterial blood circuit 1 is connected to the first connection portion α3 of the connection device La, and the connector b of the distal end of the venous blood circuit 2 is connected to the second connection portion β3 of the connection device La. The third connection portion Laa of the connection device La is connected to the to-be-connected portion γ of the connection line L13. After the connection test step in the first embodiment is performed, the control device C controls the same step as the first step in the first embodiment to be performed. Thereafter, as illustrated in FIG. 28, the control device C controls the electromagnetic valves V2, V3, V7, V8. V11, V13, V14, and V16 to be in an opened state, and controls the electromagnetic valves V1, V4, V5, V6, V9, V10, and V15 to be in a closed state. Thereafter, the control device C controls the blood pump 4 to be normally rotated and the duplex pump 7 to be rotated (the liquid level adjustment pump 11 is stopped). In this manner, the second step can be performed. In a state illustrated in FIG. 28, the control device C controls the electromagnetic valve V10 to be in an opened state and the liquid level adjustment pump 11 to be reversely rotated. In this manner, the third step can be performed. In the second and third steps, the priming solution (dialysate) supplied from the priming solution supplying line L3 flows in the arterial blood circuit 1, the dialysate flow route of the dialyzer 3, and the venous blood circuit 2, then reaches the connection device La from the distal end (connector b) of the venous blood circuit 2 via the second connection portion β3, flows in the connection line L13 from the third connection portion Laa of the connection device La, and then is discharged via the dialysate discharge line L2.

Thereafter, as illustrated in FIG. 29, the control device C controls the electromagnetic valves V1, V3, V7, V8, V11, V13, V14 and V16 to be in an opened state, and controls the electromagnetic valves V2, V4, V5, V6, V9, V10, and V15 to be in a closed state. Thereafter, the control device C controls the blood pump 4 and the liquid level adjustment pump 11 to stop the rotation, and the duplex pump 7 to be rotated. In this manner, the fourth step can be performed. In the fourth step, the priming solution (dialysate) supplied from the priming solution supplying line L3 flows in the upstream side (connector a side) from the connection portion with the priming solution supplying line L3 in the arterial blood circuit 1, then reaches the connection device La from the distal end (connector a) of the arterial blood circuit 1 via the first connection portion α3, flows in the connection line L13 from the third connection portion Laa of the connection device La, and then is discharged via the dialysate discharge line L2.

According to the above-described ninth embodiment, during the priming, the distal end of the arterial blood circuit 1 and the distal end of the venous blood circuit 2 are respectively connected to the connection line L13 via the connection device La. The priming solution (dialysate) supplied from the priming solution supplying line L3 is discharged from the distal end of the arterial blood circuit 1 and the distal end of the venous blood circuit 2 via the dialysate discharge line L2 (strictly speaking, discharged from the distal end of the arterial blood circuit 1 and the distal end of the venous blood circuit 2 via the connection line L13 and the dialysate discharge line L2). Accordingly, the priming solution used during the priming can be discharged using the dialysate discharge line L2. Therefore, the priming solution can be easily collected.

In addition, according to the above-described ninth embodiment, the dialysate discharge line L2 includes the duplex pump 7 which discharges the dialysate from the dialyzer 3 to the dialysate discharge line L2. During the priming, the distal end of the arterial blood circuit 1 and the distal end of the venous blood circuit 2 are connected to the connection line L13 located on the downstream side from the duplex pump 7 in the dialysate discharge line L2 (to be located on the downstream side from the duplex pump 7 since the electromagnetic valve V15 is in a closed state). Accordingly, it is possible to reliably avoid a case where the priming solution discharged from the distal end of the arterial blood circuit 1 and the distal end of the venous blood circuit 2 unintentionally reaches the dialyzer 3.

In particular, according to the above-described ninth embodiment, there is provided the connection device La including the first connection portion α3 and the second connection portion β3 which can be respectively connected to the distal end of the arterial blood circuit 1 and the distal end of the venous blood circuit 2, and the third connection portion Laa which can be connected to the dialysate discharge line L2 or the connection line L13. During the priming, the priming solution (dialysate) supplied from the priming solution supplying line L3 is discharged from the distal end of the arterial blood circuit 1 and the distal end of the venous blood circuit 2 to the dialysate discharge line L2 or the connection line L13 via the connection device La. Accordingly, it is possible to avoid a case where the distal end (connector a) of the arterial blood circuit 1 and the distal end (connector b) of the venous blood circuit 2 unintentionally come into contact with the dialysis device B including the dialysate discharge line L2, thereby enabling the dialysis device B to be maintained cleanly. Furthermore, since the to-be-connected portion γ on the dialysis device B is sufficient enough at one location, it is possible to achieve decreased component cost and a miniaturized apparatus.

Hitherto, the present embodiments have been described. However, the present invention is not limited to these embodiments. For example, a configuration may be adopted in which a containing bag containing physiological saline solution is provided so that a flow route connecting the containing bag and a portion between the blood pump 4 and the electromagnetic valve V1 in the arterial blood circuit 1 serves as a priming solution supplying line, and in which a valve device such as the electromagnetic valve is arranged in the priming solution supplying line and is in an opened state or off at any desired timing so as to supply the physiological saline solution serving as the priming solution.

In addition, a blood circuit may be employed which is configured so that a chamber which can isolate air and liquid in order to measure blood removing pressure is connected to between the connection portion with the priming solution supplying line L3 and the blood pump 4 in the arterial blood circuit 1. In this case, the liquid level adjustment device A may also be connected to the chamber. Similar to the arterial air trap chamber 5 and the venous air trap chamber 6, a configuration may be adopted so that the air is introduced to or discharged from an upper portion thereof.

The liquid level adjustment device A may be arranged in the dialysis device B or may be arranged at a position separate from the dialysis device B. In the present embodiments, although the liquid level adjustment device A is applied to the dialysis apparatus used during hemodialysis treatment, the liquid level adjustment device A may be applied to another apparatus which can extracorporeally circulate and purify blood of a patient (for example, blood purification apparatus used for a blood filtration dialysis method, a blood filtration method, and AFBF, and a blood plasma adsorption apparatus).

INDUSTRIAL APPLICABILITY

As long as there are provided a blood purification apparatus and a priming method for the same which can fill an arterial blood circuit and a venous blood circuit with priming solution supplied from a priming solution supplying line by operating a liquid level adjustment device at any desired timing during priming, the blood purification apparatus and the priming method for the same can also be applied to other forms and uses.

REFERENCE SIGNS LIST 1 arterial blood circuit
2 venous blood circuit
3 dialyzer (blood purification device)
4 blood pump
5 arterial air trap chamber
6 venous air trap chamber
7 duplex pump
8, 9 filtration filter
10 ultrafiltration pump
11 liquid level adjustment pump
12 arterial pressure detection sensor
13 venous pressure detection sensor
L1 dialysate introduction line
L2 dialysate discharge line
L3 priming solution supplying line
La connection device
A liquid level adjustment device
B dialysis device
C control device

The invention claimed is:
1. A blood purification apparatus comprising:
a blood circuit that includes:
an arterial blood circuit and
a venous blood circuit, wherein the blood circuit extracorporeally circulates blood of a patient from a distal end of the arterial blood circuit to a distal end of the venous blood circuit;

a blood purification device that is interposed between the arterial blood circuit and the venous blood circuit in the blood circuit, and that is configured to purify the blood flowing in the blood circuit;

a dialysate introduction line that introduces a dialysate to the blood purification device;

a dialysate discharge line that discharges the dialysate from the blood purification device;

a blood pump that is arranged in the arterial blood circuit;

a venous air trap chamber that is connected to the venous blood circuit;

a liquid level adjustment device that is connected to the venous air trap chamber, and that is configured to introduce or discharge air into or from an upper portion of the venous air trap chamber;

a control device that is configured to adjust a liquid level formed inside the venous air trap chamber to have a height at any desired position by operating the liquid level adjustment device;

a priming solution supplying line that is configured to supply a priming solution to the arterial blood circuit and the venous blood circuit during priming;

wherein during the priming, the control device is configured to fill the arterial blood circuit and the venous blood circuit with the priming solution supplied from the priming solution supplying line by operating the liquid level adjustment device at any desired timing; and wherein during the priming, the distal end of the arterial blood circuit and the distal end of the venous blood circuit are respectively connected to the dialysate discharge line or a connection line which connects the dialysate introduction line and the dialysate discharge line to each other, and wherein the distal end of the arterial blood circuit and the distal end of the venous blood circuit are configured to discharge the priming solution supplied from the priming solution supplying line via the dialysate discharge line.

2. The blood purification apparatus according to claim 1, wherein the distal end of the arterial blood circuit and the distal end of the venous blood circuit are respectively configured to be brought into a released state during the priming, and wherein the distal end of the arterial blood circuit and the distal end of the venous blood circuit are configured to discharge the priming solution supplied from the priming solution supplying line.

3. The blood purification apparatus according to claim 1, wherein the dialysate discharge line includes a pump which is configured to discharge the dialysate from the blood purification device to the dialysate discharge line, and wherein the distal end of the arterial blood circuit and the distal end of the venous blood circuit are configured to be connected to the dialysate discharge line or to a downstream side from the pump in the connection line during the priming.

4. The blood purification apparatus according to claim 1, further comprising: a connection device that includes: a first connection portion and a second connection portion which are configured to be respectively connected to the distal end of the arterial blood circuit and the distal end of the venous blood circuit, and a third connection portion which is configured to be connected to the dialysate discharge line or the connection line, wherein the distal end of the arterial blood circuit and the distal end of the venous blood circuit are configured to discharge the priming solution supplied from the priming solution supplying line to the dialysate discharge line or the connection line via the connection device during the priming.

5. The blood purification apparatus according to claim 3, further comprising: a connection device that includes: a first connection portion and a second connection portion which are configured to be respectively connected to the distal end of the arterial blood circuit and the distal end of the venous blood circuit, and a third connection portion which is configured to be connected to the dialysate discharge line or the connection line, wherein the distal end of the arterial blood circuit and the distal end of the venous blood circuit are configured to discharge the priming solution supplied from the priming solution supplying line to the dialysate discharge line or the connection line via the connection device during the priming.

6. The blood purification apparatus according to claim 5, wherein the liquid level adjustment device includes a liquid level adjustment pump which is configured to perform normal rotation and reverse rotation, and wherein during the priming, the control device is configured to introduce or discharge air to or from an upper portion of the venous air trap chamber by rotating the liquid level adjustment pump at any desired timing.

7. The blood purification apparatus according to claim 1, wherein the liquid level adjustment device includes a liquid level adjustment pump which is configured to perform normal rotation and reverse rotation, and wherein during the priming, the control device is configured to introduce or discharge air to or from an upper portion of the venous air trap chamber by rotating the liquid level adjustment pump at any desired timing.

8. The blood purification apparatus according to claim 1, wherein an arterial air trap chamber is connected to the arterial blood circuit, and the liquid level adjustment device is connected to each of the arterial air trap chamber and the venous air trap chamber, and wherein the control device is configured to adjust each liquid level formed inside the arterial air trap chamber and the venous air trap chamber to have the height at any desired position.

9. The blood purification apparatus according to claim 1, wherein the priming solution supplying line is configured so that one end is connected to the dialysate introduction line and another end is connected to a predetermined portion of the blood circuit, and the priming solution supplying line is configured to supply the dialysate of the dialysate introduction line to the arterial blood circuit and the venous blood circuit.

10. The blood purification apparatus according to claim 1, wherein the liquid level adjustment device is configured to discharge the priming solution from the venous air trap chamber.

11. The blood purification apparatus according to claim 1, wherein the apparatus includes a duplex pump which is connected to the dialysate introduction line and the dialysate discharge line and connects the dialysate introduction line and the dialysate discharge line to each other.

* * * * *